(12) United States Patent
Cho et al.

(10) Patent No.: US 10,626,447 B2
(45) Date of Patent: Apr. 21, 2020

(54) METHODS AND COMPOSITIONS OF NON-ENZYMATIC AMPLIFICATION AND DIRECT DETECTION OF NUCLEIC ACIDS

(71) Applicant: CROSSLIFE TECHNOLOGIES INC., Carlsbad, CA (US)

(72) Inventors: HyunDae Cho, San Marcos, CA (US); Chang Hee Kim, San Marcos, CA (US)

(73) Assignee: CROSSLIFE TECHNOLOGIES INC., Carlsbad, CA (US)

( * ) Notice: Subject to any disclaimer, the term of this patent is extended or adjusted under 35 U.S.C. 154(b) by 472 days.

(21) Appl. No.: 15/068,371

(22) Filed: Mar. 11, 2016

(65) Prior Publication Data

US 2016/0266118 A1 Sep. 15, 2016

Related U.S. Application Data

(60) Provisional application No. 62/132,568, filed on Mar. 13, 2015.

(51) Int. Cl.

| | |
|---|---|
| *C12Q 1/68* | (2018.01) |
| *C12Q 1/6809* | (2018.01) |
| *G01N 33/569* | (2006.01) |
| *C12Q 1/686* | (2018.01) |
| *C12Q 1/6804* | (2018.01) |

(52) U.S. Cl.
CPC ......... *C12Q 1/6809* (2013.01); *C12Q 1/6804* (2013.01); *C12Q 1/686* (2013.01); *G01N 33/56983* (2013.01)

(58) Field of Classification Search
CPC ........ C12Q 2525/107; C12Q 2525/161; C12Q 2563/107; C12Q 2563/131; C12Q 2563/137; C12Q 2563/155; C12Q 2565/1015; C12Q 1/686; C12Q 1/6804; C12Q 2531/113; C12Q 2565/629; C12Q 1/6809; G01N 33/56983
USPC ................................................ 435/91.2, 6.11
See application file for complete search history.

(56) References Cited

U.S. PATENT DOCUMENTS

| | | | | |
|---|---|---|---|---|
| 8,323,888 B2 * | 12/2012 | Mirkin | .................... | B82Y 15/00 435/6.1 |
| 2014/0094383 A1 * | 4/2014 | Lee | .................... | G01N 33/5432 506/9 |

OTHER PUBLICATIONS

Metelev, VG. Et al. (1999) "Oligodeoxyribonucleotides with Internucleotidic or Terminal Phosphorothioate Groups: Different Pathways in the Reaction with Water-Soluble Carbodhmide." Nucleosides & Nucleotides vol. 18, 1999, p. 2711.

Luebke KJ, Dervan PB. (1992) "Nonenzymatic ligation of oligodeoxyribonucleotides on a duplex DNA template by triple-helix formation." Nucleic Acids Res. Jun. 25;20(12):3005-9.
Shabarova ZA, Merenkova IN, Oretskaya TS, Sokolova NI, Skripkin EA, Alexeyeva EV, Balakin AG, Bogdanov AA. (1991) "Chemical ligation of DNA: the first non-enzymatic assembly of a biologically active gene." Nucleic Acids Res. Aug. 11;19(15):4247-51.
Xu Y, Karalkar NB, Kool ET. (2001) "Nonenzymatic autoligation in direct three-color detection of RNA and DNA point mutations." Nat Biotechnol. Feb;19(2):148-52.
Rubin E, Rumney S 4th, Wang S, Kool ET. (1995) "Convergent DNA synthesis: a non-enzymatic dimerization approach to circular oligodeoxynucleotides." Nucleic Acids Res. Sep. 11;23(17):3547-53.
Gryaznov SM, Letsinger RL. (1993) "Template controlled coupling and recombination of oligonucleotide blocks containing thiophosphoryl groups." Nucleic Acids Res. Mar. 25;21(6):1403-8.
Xu Y, Kool ET. (1997) "A Novel 5'-Iodonucleoside Allows Efficient Nonenzymatic Ligation of Single-stranded and Duplex DNAs." Tetrahedron Lett. Aug. 11;38(32):5595-5598.
Xu Y, Kool ET. (1998) "Chemical and enzymatic properties of bridging 5'-S-phosphorothioester linkages in DNA." Nucleic Acids Res. Jul. 1;26(13):3159-64.
Marshall A, Hodgson J. "DNA chips: an array of possibilities." Nat Biotechnol. Jan. 1998;16(1):27-31.
Zhang B, Wang Q, Pan X. "MicroRNAs and their regulatory roles in animals and plants." J Cell Physiol. Feb. 2007;210(2):279-89.
Li X, Zhan ZYJ, Knipe R, Lynn DG. J. Am. Chem. Soc. 2002;124:746-747.
T. N. Grossmann, O. Seitz,(2006) "DNA-catalyzed transfer of a reporter group." J. Am. Chem. Soc. 2006, 128, 15596-15597.
T. N. Grossmann, L. Roglin, O. Seitz, (2008) "Achieving Turnover in DNA-Templated Reactions ." Angew. Chem. Int. Ed. 47, 7119-7122.
Grossmann TN, Röglin L, Seitz O. (2008) "Target-Catalyzed Transfer Reactions for the Amplified Detection of RNA." Angew Chem Int Ed Engl. ;47(37):7119-22.
X. H. Chen, A. Roloff, O. Seitz, (2012) "Consecutive Signal Amplification for DNA Detection Based on De Novo Fluorophore Synthesis and Host-Guest Chemistry." Angew. Chem. Int. Ed., 51, 4479-4483.
Vázquez O, Seitz O. (2014) Templated native chemical ligation: peptide chemistry beyond protein synthesis. J Pept Sci. Jan. 7.
World Health Organization. (2009) "Dengue: guidelines for diagnosis, treatment, prevention and control." WHO Press, Geneva, Switzerland.

(Continued)

*Primary Examiner* — Jezia Riley
(74) *Attorney, Agent, or Firm* — Knobbe, Martens, Olson & Bear LLP

(57) ABSTRACT

The detection and quantification of nucleic acid sequences can be done using template catalyzed TARA transfer reactions without enzyme and PCR. It comes with the novel chemistry platform technology using Template Assisted Rapid Assay (TARA), an enzyme-free, PCR-less and rapid transfer reaction assay directly from samples from nasopharyngeal swab, nasal aspirate, oropharyngeal swab or blood. The procedures of the detection and quantification of nucleic acid sequences include utilizing two or more oligonucleotide probes that reversibly bind a target nucleic acid in close proximity to each other and possess complementary reactive TARA reaction moieties. In addition, various methods, reagents, and kits for detecting and quantifying nucleic acid sequences and for determining the sequence of nucleic acids are provided.

25 Claims, 15 Drawing Sheets
(15 of 15 Drawing Sheet(s) Filed in Color)

(56) References Cited

OTHER PUBLICATIONS

Halstead SB, Nimmannitya S, Cohen SN. (1970) "Observations related to pathogenesis of dengue hemorrhagic fever. IV. Relation of disease severity to antibody response and virus recovered." Yale J. Biol. Med. 42:311-328.
Martina BEE, Koraka P, Osterhaus AD. (2009) "Dengue virus pathogenesis: an integrated view." Clin. Microbiol. Rev. 22:564-581.
Ellis J, Iturriza M, Allen R, Bermingham A, Brown K, Gray J, Brown D. (2009) "Evaluation of four real-time PCR assays for detection of influenza A(H1N1) viruses." Euro Surveill. Jun. 4;14(22). pii: 19230.
Waggoner JJ, et al. (2013) "Development of an internally controlled real-time reverse transcriptase PCR assay for pan-dengue virus detection and comparison of four molecular dengue virus detection assays." J Clin Microbiol. Jul. 2013;51(7):2172-81.
Alexander N, Balmaseda A, Coelho IC, Dimaano E, Hien TT, et al. (2011) "Multicentre prospective study on dengue classification in four South-east Asian and three Latin American countries." Trop Med Int Health 16(8):936-48.
Blacksell SD, et al. (2012) "Comparison of performance of serum and plasma in panbio dengue and Japanese encephalitis virus enzyme-linked immunosorbent assays." Am J Trop Med Hyg. Sep;87(3):573-5.
Blacksell SD, et.al., (2012) "Comparison of seven commercial antigen and antibody enzyme-linked immunosorbent assays for detection of acute dengue infection." Clin Vaccine Immunol. May;19(5):804-10.
Blacksell SD. (2012) "Commercial dengue rapid diagnostic tests for point-of-care application: recent evaluations and future needs?" J Biomed Biotechnol.:151967. doi: 10.1155/2012/151967. Epub May 10, 2012. Review.
TDR/WHO. "Evaluation of commercially available antidengue virus immunoglobulin M tests." Diagnostics Evaluation Series No. 3 [online] <http://apps.who.int/ tdr/publications/tdr-research-publications/diagnostics evaluation- 3/pdf/diagnostics evaluation-3.pdf> (TDR/WHO, Geneva. Switzerland, 2009).
Hunsperger E. et al. "Evaluation of commercially available anti-dengue virus immunoglobulin M tests." Emerg. Infect. Dis. 15,436-440 (2009).
Mackay IM, Arden KE, Nitsche A (2002) "Real-time PCR in virology." Nucleic Acids Res 30: 1292-1305.
TDR/WHO. Dengue diagnostics: Proceedings of an international workshop Oct. 4-6, 2004. [online] <http://apps.who.int/tdr/publications/tdrresearch- publications/dengue-diagnosticsproceedings/pdf/dengue_diagnostics.
Santiago GA, et.al., (2013) "Analytical and clinical performance of the CDC real time RT-PCR assay for detection and typing of dengue virus." PLoS Negl Trop Dis. Jul. 11;7(7), pp. 1-15.
Waggoner JJ, et.al., (2013) "Comparison of the FDA-approved CDC DENV-1-4 real-time reverse transcription-PCR with a laboratory-developed assay for dengue virus detection and serotyping." J Clin Microbiol. Oct;51(10):3418-20.
Teoh BT, Sam SS, Tan KK, Johari J, Danlami MB, Hooi PS, Md-Esa R, AbuBakar S., (2013) "Detection of dengue viruses using reverse transcription-loop-mediated isothermal amplification." BMC Infect Dis. Aug. 21;13:387.
Parida M, Horioke K, Ishida H, Dash PK, Saxena P, Jana AM, Islam MA, Inoue S, Hosaka N, Morita K. (2005) "Rapid detection and differentiation of dengue virus serotypes by a real-time reverse transcription-loop-mediated isothermal amplification assay." J Clin Microbiol. Jun. 2005;43(6):2895-903.

Peeling RW, et.al., (2010) "Evaluation of diagnostic tests: dengue." Nat Rev Microbiol. Dec;8 (12 Suppl):S30-8. Review.
Guzman MG, et.al., (2010) "Dengue: a continuing global threat." Nat Rev Microbiol. Dec. 2010;8(12 Suppl):S7-16. doi: 10.1038/nrmicro2460. Review.
Guan Y, Smith GJ, Webby R, Webster RG. (2009) "Molecular epidemiology of H5N1 avian influenza." Rev. Sci. Tech;28(1):39-47.
Peiris JS, Poon LL, Guan Y. (2009) "Emergence of a novel swine-origin influenza A virus (S-OIV) H1N1 virus in humans." J. Clin. Virol;45(3):169-173.
World Health Organization (2009) Statement to the press by WHO Director-General Dr Margaret Chan. Available: http://www.who.int/mediacentre/ news/statements/2009/ h1n1_pandemic_phase6_20090611/en/index.html. Accessed on Aug. 15, 2009.
Levy-Bruhl D, Vaux S (2009) Modified surveillance of influenza A(H1N1)v virus infections in France. Euro Surveill.
Van der Vries E, Schutten M. (2010) "Satisfying the need for rapid diagnosis of new variant influenza A H1N1." Expert Rev Mol Diagn. Apr;10(3):251-3.
Vasoo S, Stevens J, Singh K. (2009) "Rapid antigen tests for diagnosis of pandemic (Swine) influenza A/H1N1." Clin Infect Dis. Oct. 1;49(7):1090-3.
Ganzenmueller T, Kluba J, Hilfrich B, Puppe W, Verhagen W, Heim A, Schulz T, Henke-Gendo C. (2010) "Comparison of the performance of direct fluorescent antibody staining, a point-of-care rapid antigen test and virus isolation with that of RT-PCR for the detection of novel 2009 influenza A (H1N1) virus in respiratory specimens." J Med Microbiol. Jun;59(Pt 6):713-7.
Karre T, Maguire HF, Butcher D, Graepler A, Weed D, Wilson ML. (2010) "Comparison of Becton Dickinson Directigen EZ Flu A+B test against the CDC real-time PCR assay for detection of 2009 pandemic influenza A/H1N1 virus." J Clin Microbiol. Jan;48(1):343-4.
CDC, "Evaluation of rapid influenza diagnostic tests for detection of novel influenza A (H1N1) Virus—United States", 2009. MMWR Morb Mortal Wkly Rep 58: 826-829.
Uyeki T (2009) "Diagnostic testing for 2009 pandemic influenza A (H1N1) virus infection in hospitalized patients." N Engl J Med 361: e114.
Kok J, Blyth CC, Foo H, Patterson J, Taylor J, et al. (2010) "Comparison of a rapid antigen test with nucleic acid testing during cocirculation of pandemic influenza A/H1N1 2009 and seasonal influenza A/H3N2." J Clin Microbiol 48: 290-291.
Faix DJ, Sherman SS, Waterman SH (2009) "Rapid-test sensitivity for novel swine-origin influenza A (H1N1) virus in humans." N Engl J Med 361: 728-729.
Hurt AC, Baas C, Deng YM, Roberts S, Kelso A, et al. (2009) "Performance of influenza rapid point-of-care tests in the detection of swine lineage A(H1N1) influenza viruses." Influenza Other Respi Viruses 3: 171-176.
CDC, "Performance of rapid influenza diagnostic tests during two school outbreaks of 2009 pandemic influenza A(H1N1) virus infection—Connecticut", 2009. MMWR Morb Mortal Wkly Rep 58: 1029-1032.
Chan KH, Lai ST, Poon LL, Guan Y, Yuen KY, et al. (2009) "Analytical sensitivity of rapid influenza antigen detection tests for swine-origin influenza virus (H1N1)." J Clin Virol 45: 205-207.
Hawkes M, Richardson Se, Ipp M, Schuh S, Adachi D, et al. (2010) "Sensitivity of rapid influenza diagnostic testing for swine-origin 2009 a (H1N1) influenza virus in children." Pediatrics 125: e639-644.
Andresen DN, Kesson AM (2010) "High sensitivity of a rapid immunochromatographic test for detection of influenza A virus 2009 H1N1 in nasopharyngeal aspirates from young children." J Clin Microbiol 48: 2658-2659.

\* cited by examiner

FIGURE 1  Template Assisted Rapid Assay

FIGURE 6
Lateral Flow Assay (LFA)
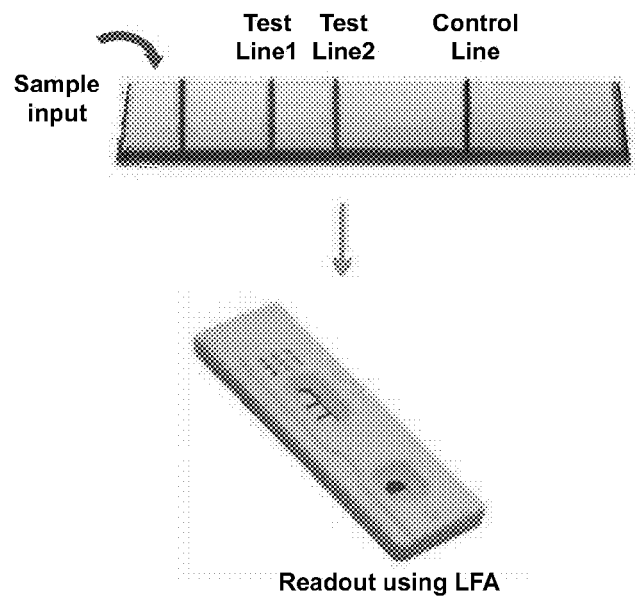
Multi-Channel LFA
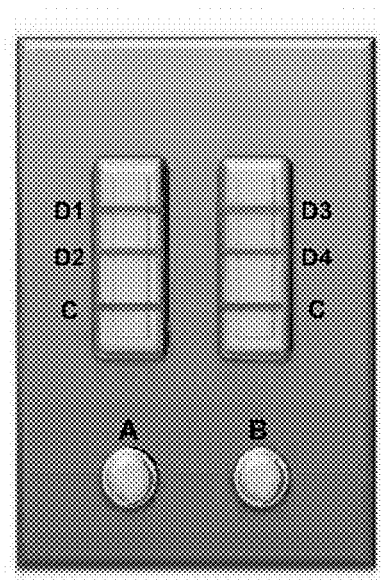

FIGURE 8A
FIGURE 8B
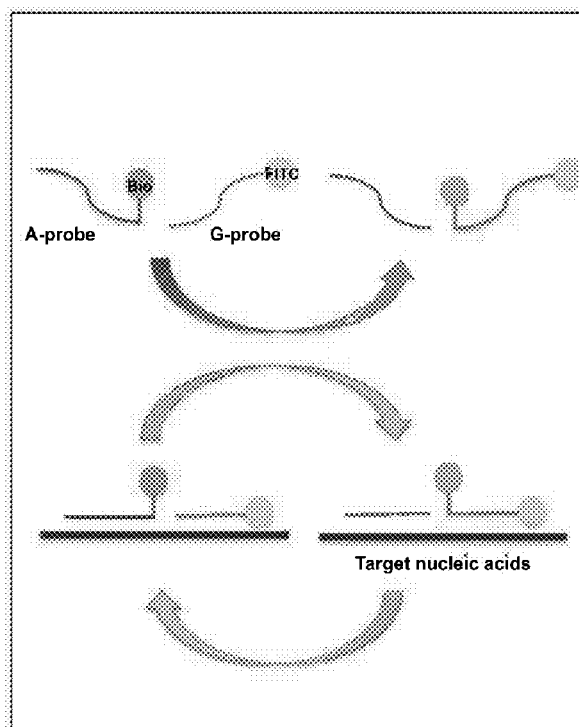
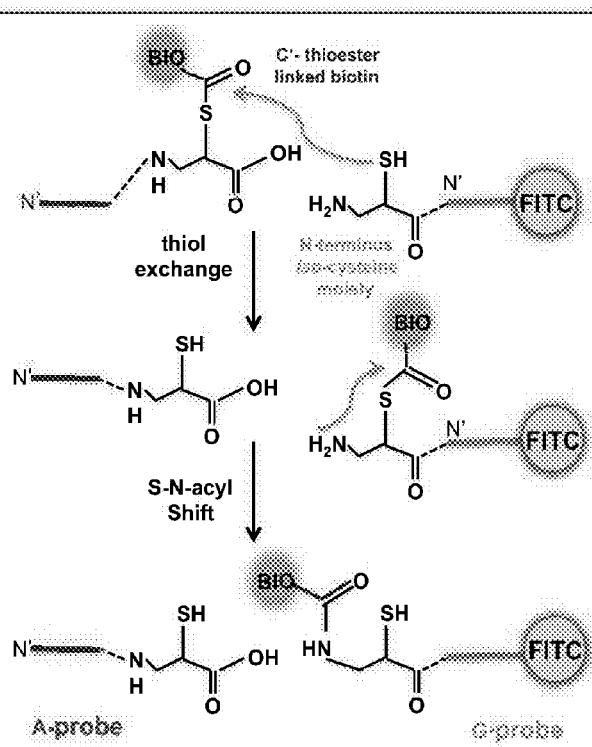

FIGURE 10A
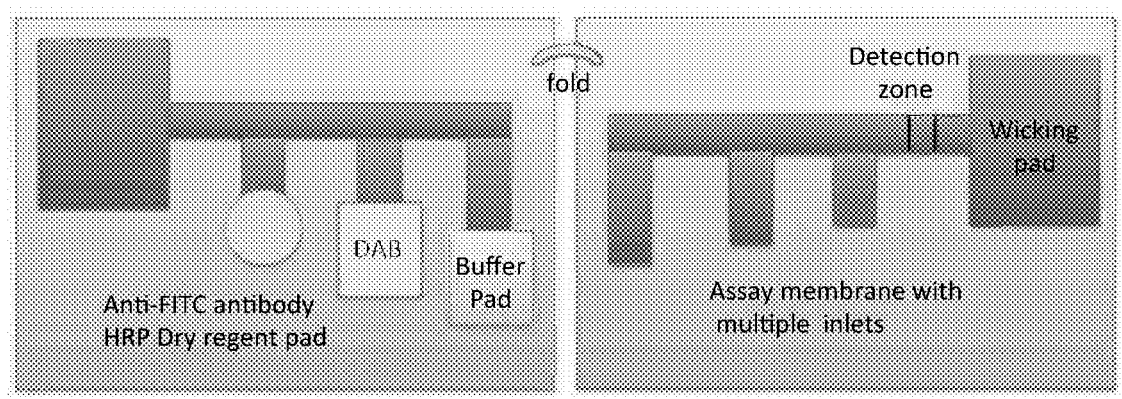
TARA assay card with dry reagents
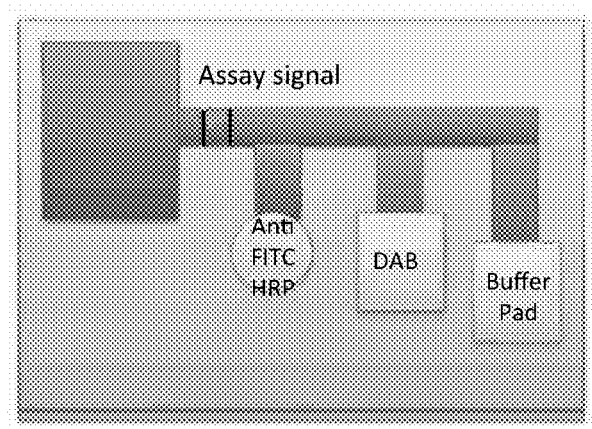
Folded 2DPN TARA assay card
FIGURE 10B

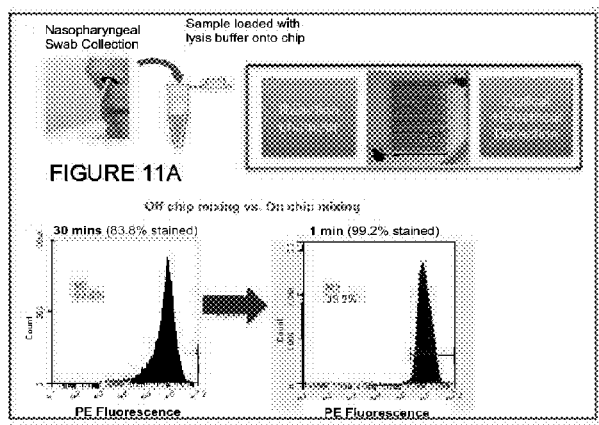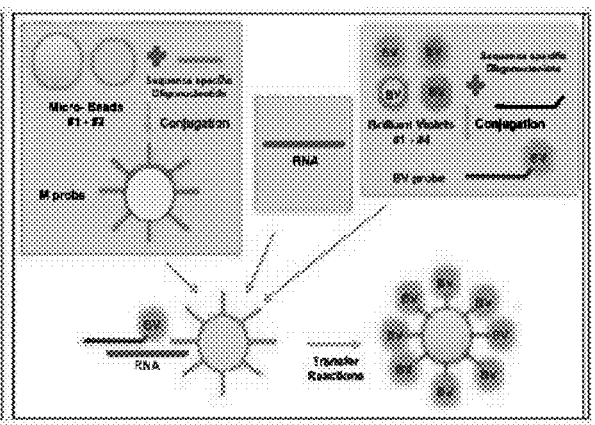
FIGURE 11A
FIGURE 11B
FIGURE 11C

FIGURE 12A  FIGURE 12B  FIGURE 12C  FIGURE 12D
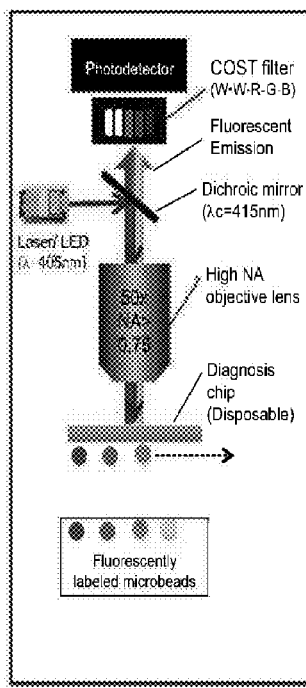
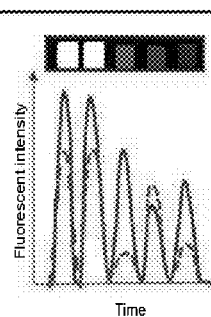
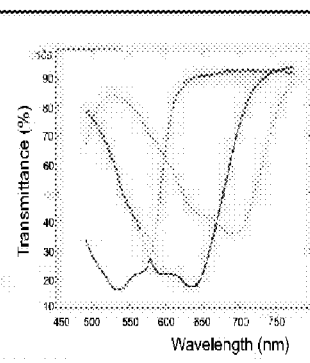
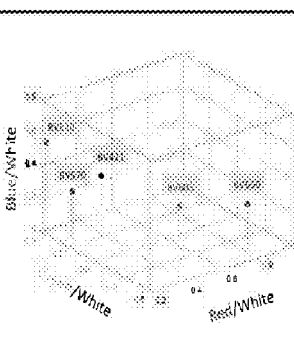
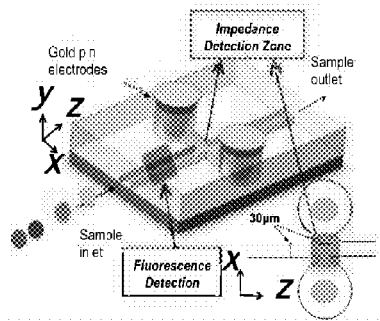
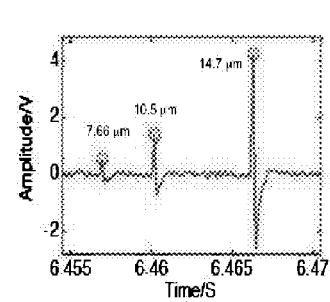
FIGURE 12E  FIGURE 12F FIGURE 13A
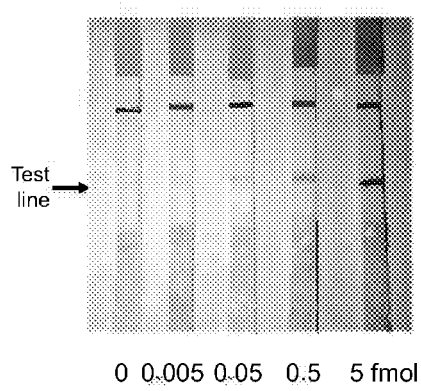
Test line →
0  0.005  0.05  0.5  5 fmol
FIGURE 13B
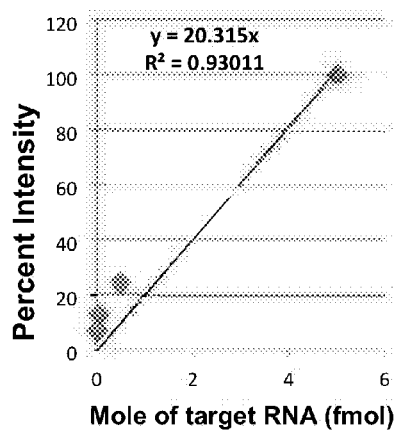
$y = 20.315x$
$R^2 = 0.93011$
Mole of target RNA (fmol)
FIGURE 13C
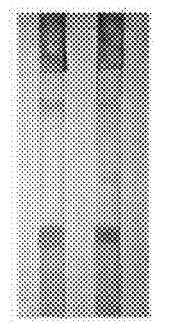
Plasma   Plasma
No virus  Virus
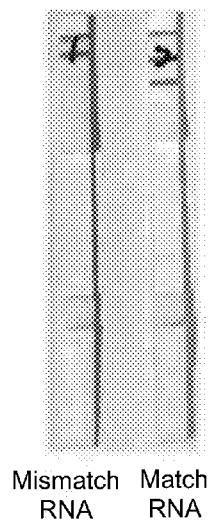
Mismatch  Match
RNA       RNA
FIGURE 13D
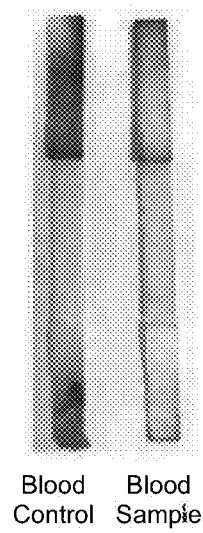
Blood     Blood
Control   Sample
FIGURE 13E
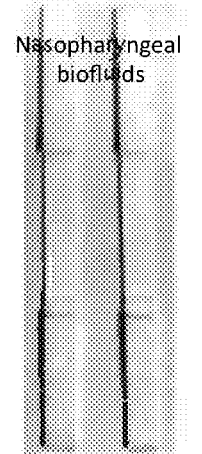
Nasopharyngeal biofluids
Control  Sample
FIGURE 13F
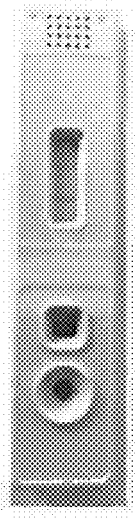
FIGURE 13G FIGURE 14A
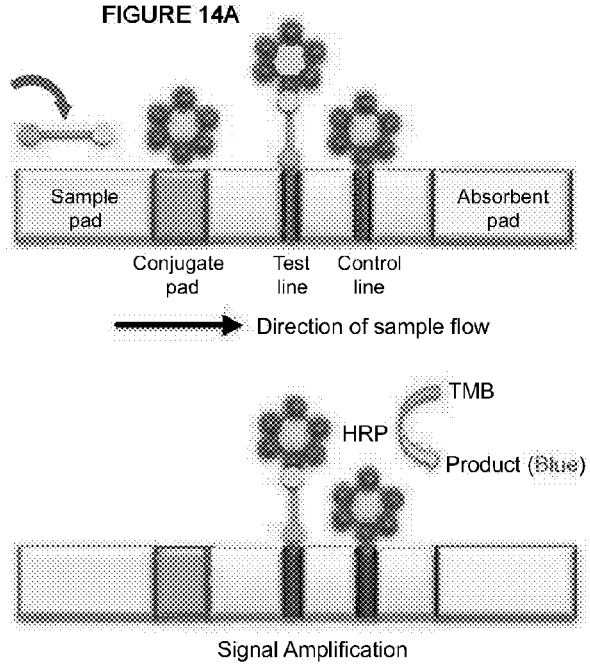
Signal Amplification
FIGURE 14B
Not amplified
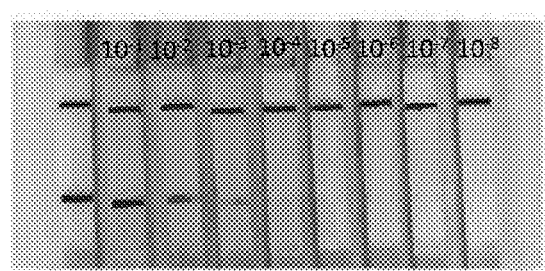
Amplified after HRP with TMB
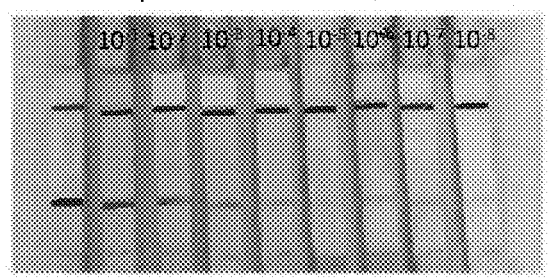

METHODS AND COMPOSITIONS OF NON-ENZYMATIC AMPLIFICATION AND DIRECT DETECTION OF NUCLEIC ACIDS

STATEMENT REGARDING FEDERALLY SPONSORED R&D

This invention was made with government support 1R43TR001271-01 awarded by National Center for Advancing Translational Sciences (NCATS), National Institutes of Health (NIH), The U.S. Department of Health and Human Services (HHS). The government has certain rights to the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present disclosure is generally in the technical field of nucleic acid molecule detection that can be implemented, for example on a paper strip or microfluidics device, without nucleic acid extraction or amplification thereof, e.g. via a polymerase chain reaction (PCR). In some embodiments, the detection system can be used substantially near the point of care (POC) so that patients can be treated rapidly and at low cost. More particularly, the present disclosure relates to methods, compositions, systems, and kits for detecting one or more target sequences and, in some embodiments, can be applied in the POC setting. In one aspect, a novel method for detecting and performing multiplex nucleic acid detection without nucleic acid extraction, or amplification thereof are provided. In some embodiments, a sensitive nucleic acid POC diagnostic paper dipstick or microfluidic device is provided that is capable of detecting and identifying all of cancers or all of infectious diseases such as the dengue virus, influenza virus, chikungunya virus, and malaria etc. In some other embodiments, the method is configured such that the target nucleic acid sequence for the method is associated with one or more selected from the group consisting of dengue virus, influenza virus, chikungunya virus, the human immunodeficiency virus (HIV), the Hepatitis C virus (HCV), Human papillomavirus (HPV), Middle East Respiratory Syndrome (MERS) virus, arboviruses, methicillin-resistant staphylococcus aureus (MRSA); a bacterium, a fungus, and a parasite. In some other embodiments, the target nucleic acid sequence is associated with nucleic acid biomarkers selected from the group consisting of RNA, DNA, and microRNA in non-communicable and/or chronic diseases.

Description of the Related Art

A number of non-enzymatic or template mediated chemical ligation methods have been developed that can be used to detect sequence variations. These include chemical ligation methods that utilize coupling reagents, such as N-cyanoimidazole, cyanogen bromide, and 1-ethyl-3-(3-dimethylaminopropyl)-carbodiimide hydrochloride. Kool (U.S. Pat. No. 7,033,753), which is incorporated herein by reference in its entirety, describes the use of chemical ligation and fluorescence resonance energy transfer (FRET) to detect genetic polymorphisms. Other chemical ligation methods react a 5'-tosylate or 5'-iodo group with a 3'-phosphorothioate group, resulting in a DNA structure with a sulfur replacing one of the bridging phosphodiester oxygen atoms.

Some of the advantages of using non-enzymatic approaches for nucleic acid target detection include lower sensitivity to non-natural DNA analog structures, ability to use RNA target sequences, lower cost and greater robustness under varied conditions. Letsinger et al. (U.S. Pat. No. 5,780,613, herein incorporated by reference in its entirety) have previously described an irreversible, nonenzymatic, covalent autoligation of adjacent, template-bound oligonucleotides wherein one oligonucleotide has a 5' displaceable group and the other oligonucleotide has a 3' thiophosphoryl group.

PCT applications WO 95/15971, PCT/US96/09769, PCT/US97/09739, PCT US99/01705, WO96/40712 and WO98/20162, all of which are expressly incorporated herein by reference in their entirety, describe compositions comprising nucleic acids containing electron transfer moieties, including electrodes, which allow for novel detection methods of nucleic acid hybridization. One technology that has gained increased prominence involves the use of DNA arrays, especially for applications involving simultaneous measurement of numerous nucleic acid targets.

SUMMARY OF THE INVENTION

In one aspect, a method of determining the presence and/or level of an analyte comprising a target nucleic acid sequence in a sample is provided. The method may comprise contacting the sample with a mixture comprising at least one set of probes to provide a reaction mixture, the at least one set of probes comprising: a) a plurality of a first probe, the first probe comprising a first reporter which is capable of being transferred to a second probe, and a first nucleic acid region, said first nucleic acid region being complementary to a first part of the target nucleic acid sequence, and b) a plurality of a second probe, the second probe comprising a second nucleic acid region complementary to a second, different part of the target nucleic acid sequence, wherein said first part and said second part of the target nucleic acid sequence are substantially adjacent to each other in the target nucleic acid sequence, wherein the plurality of second probes is associated with one or more nano- or micro-particles, and wherein, in the presence of the target nucleic acid sequence, the first reporter group in the first probe is transferred to the second probe. The method may further comprise measuring the presence and/or level of the first reporter group that has been transferred to the second probe.

In some embodiments, the target nucleic acid sequence is not amplified prior to contacting the sample with the mixture.

In some other embodiments, the method may further comprise: isolating the second probe to which the first reporter group was transferred prior to measuring.

In still some other embodiments, the one or more of the nano- or micro-particles may comprise a gold nanoparticle, a silver nanoparticle, or a microbead.

In still some other embodiments, the second probe may comprise a second reporter group such that the presence and/or level of the first reporter group that has been transferred to the second probe may be measured by measuring the presence and/or level of coexistence of the first reporter and the second reporter on the second probe.

In still some other embodiments, the probe set may further comprise a third probe, which comprises a third nucleic acid region which is complementary to a third part of the target nucleic acid sequence, the third probe optionally comprising a third reporter group, wherein said third part is substantially adjacent to the first part or the second part of the target nucleic acid sequence.

In still some other embodiments, the one or more reporter groups are selected from the group consisting of a fluorescent moiety, a quenching moiety, a donor fluorescent moiety, an acceptor fluorescent moiety capable to fluoresce upon transfer of energy from a donor fluorescent moiety, a radioactive moiety, and a binding moiety.

In still some other embodiments, the distance between the first part and the second part of the target nucleic acid sequence may be from 0 to 10 nucleotides.

In still some other embodiments, the method comprises contacting the sample with one or more additional set of probes, each additional set of probes being configured to hybridize to a different target nucleic acid sequence.

In still some other embodiments, each additional set of probes utilizes a different size of nano- or micro-particle.

In still some other embodiments, each additional set of probes utilizes a different reporter.

In still some other embodiments, the method is implemented in a lateral flow assay device or a two-dimensional paper network device comprising a reaction mixture receiving zone and a detection zone.

In still some other embodiments, the presence and/or level of the first reporter is measured in the detection zone.

In still some other embodiments, the method is implemented in a microfluidic device.

In still some other embodiments, the reaction mixture is provided to a microfabricated channel and the presence and/or level of the first reporter transferred from the first probe to the second probe is measured by a detector operably linked to the microfluidic device.

In still some other embodiments, the method is carried out without nucleic acid extraction, amplification and reverse transcription.

In still some other embodiments, the sample comprises one or more of a nasopharyngeal swab, nasal aspirate, an oropharyngeal swab, and blood obtained from the subject.

In another aspect, a kit for determining the presence and/or level of a target nucleic acid sequence in a sample is provided. The kit may comprise a) a plurality of a first probe, the first probe comprising a first reporter which is capable of being transferred to a second probe, and a first nucleic acid region that is complementary to a first part of the target nucleic acid sequence, and b) a plurality of a second probe, the second probe comprising a second nucleic acid region complementary to a second, different part of the target nucleic acid sequence, wherein said first part and said second part of the target nucleic acid sequence are substantially adjacent to each other in the target nucleic acid sequence, wherein the plurality of second probes is associated with one or more nano- or micro-particles, and wherein the first and second probes are configured such that when the first and second probes are bound to the first and second parts of the target nucleic acid sequence the first reporter group in the first probe is transferred to the second probe.

In some embodiments, the one or more nano- or micro-particles is selected from the group consisting of a gold nanoparticle, a silver nanoparticle, a microbead, and a mixture thereof.

In still another aspect, a method of diagnosing a condition in a subject in or substantially near a point of care is provided. The method may comprise providing a sample obtained from the subject, wherein said sample may comprise a target nucleic acid sequence associated with the condition; contacting the sample with a mixture, said mixture comprising at least one set of probes comprising: a) a plurality of a first probe, the first probe comprising a first reporter which is capable of being transferred to a second probe, and a first nucleic acid region complementary to a first part of the target nucleic acid sequence, and b) a plurality of a second probe, the second probe comprising a second nucleic acid region complementary to a second, different part of the target nucleic acid sequence, wherein said first part and said second part of the target nucleic acid sequence are substantially adjacent to each other in the target nucleic acid sequence, wherein the plurality of second probe is associated with one or more nano- or micro-particles; wherein, in the presence of the target nucleic acid sequence, the first reporter group in the first probe is transferred to the second probe. The method may further comprise measuring the presence and/or level of the first reporter group that has been transferred to the second probe, wherein the target nucleic acid sequence is not amplified prior to contacting the sample with the mixture.

In some embodiments, the method further comprises: isolating the second probe to which the plurality of the first reporter group was transferred.

In some other embodiments, the target nucleic acid sequence is associated with one or more selected from the group consisting of dengue virus, influenza virus, chikungunya virus, the human immunodeficiency virus (HIV), the Hepatitis C virus (HCV), Human papillomavirus (HPV), Middle East Respiratory Syndrome (MERS) virus, arboviruses, and methicillin-resistant staphylococcus aureus (MRSA).

In still some other embodiments, the target nucleic acid sequence is associated with one or more selected from the group consisting of a bacterium, a fungus and a parasite.

In still some other embodiments, the target nucleic acid sequence is associated with nucleic acid biomarkers selected from the group consisting of RNA, DNA, and microRNA in non-communicable and/or chronic diseases.

In still some other embodiments, the sample comprises one or more selected from the group consisting of nasopharyngeal swab, nasal aspirate, oropharyngeal swab, and blood obtained from the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various aspects of the invention will become apparent and more readily appreciated from the following description of the embodiments, taken in conjunction with the accompanying drawings in which:

FIG. 6 shows schematic diagrams illustrating a lateral flow assay design. The lateral flow assay is designed to detect specific antibody-attached gold nanoparticles according to some embodiments of the invention.

FIG. 8A shows schematic diagrams illustrating a general principle of TARA reactions according to some embodiments of the invention. G-probe (5'-cysteine moiety) is shown in orange, A-probe (3'-thioester-link, and a biotin group) is in blue, and the dark blue line shows target nucleic acids. In FIG. 8B the principle of template assisted transfer reactions illustrated in this particular embodiment involves the transfer of a reporter group by a native chemical ligation-like reaction. The reporter group, e.g. the blue circled A (antigen, antibody or biotin) is first transferred to a thiol group of the acceptor G-probe (gold nanoparticle-linked PNA probe), and then in an irreversible intramolecular reaction to an amino group of the acceptor G-probe.).

FIG. 9A. Preparation of HRP-GNP PNA conjugates. The reporter group includes, for example, antigen, antibody or biotin. The transfer reaction system involves two reactive PNA probes: a 3'-thiolated PNA (A probe) and the acceptor PNA (G probe) that is equipped with a cysteine moiety at the 5'-end. The G probe has a FITC at the 3'end. FIG. 9B. Conjugation of GNP-HRP on the conjugation pad to PNA and capture of GNP-HRP-PNA conjugates on lateral flow strip using the reporter group (in this case biotin) and its complement (streptavidin). FIG. 9C. Signal enhancement using the substrate AEC: 3-amino 9-ethylcarbazole in a lateral flow assay design. The lateral flow assay, at least in this particular embodiment, is designed to detect specific reporter group-attached gold nanoparticles. FIG. 9D. Alternative approach for enhancing the detection limit (up to 105) is to use both a dual gold nanoparticle conjugate-based lateral flow assay and silver enhancement according to some embodiments of the invention.

FIGS. 10A and 10B illustrate schematic diagrams illustrating 2DPN TARA device with incorporated dry reagents for automated ELISA according to some embodiments of the invention. FIG. 10A Folding 2DPN device showing assay membrane on one side with three inlets for sequential reagent delivery, and glass fiber pads containing dry-preserved HRP labeled secondary antibody, DAB and buffer on the other side, assembled on a Mylar laminate material. In some embodiments, malarial antigen spiked in fetal bovine serum and buffer containing hydrogen peroxide is added to rehydrate the dry HRP-antibody and DAB respectively. The device is folded to simultaneously activate the reagent flow through the device. FIG. 10B Folded device showing malarial sandwich immunoassay signal development. A streak of DAB precipitate is seen near the first inlet. This is due to the two reagents (HRP-antibody and DAB substrate) flowing back to back. This however did not have a negative impact on the assay. Streaking could be eliminated by adding a wash step between the HRP-antibody and DAB delivery.

FIGS. 11A, 11B, and 11C show schematic diagrams illustrating some embodiments where TARA reactions are implemented in a microfluidic chip device. FIG. 11A Integrated microfluidic chip and automated chip prototype. FIG. 11B Using micromixer, only 1 min, more than 99% of live cells are stained fluoresce labeled antibodies whereas "off-chip" labeling took more than 30 mins to reach 83.3% labeling efficiencies. FIG. 11(C) Template Assisted Rapid Assay (TARA). RNA-assisted Brilliant Violet-Dye transfer on a magnetic microbead.

FIGS. 12A, 12B, 12C, 12D, 12E, and 12F show schematic diagrams illustrating the demonstration of Color-Space-Time (COST) coding design according to some embodiments of the invention. FIG. 12A Each fluorescently labeled particle image is magnified by 50× and the image is projected onto a color filter array in front of a photodetector. FIG. 12B The COST color filter is designed to have discrete regimes. The first two transparent slits are used to estimate panicle's travel velocity and set the absolute intensity or each fluorophore. FIG. 12C Transmission spectra or three color filters using in the COST detection setup. Note that each color filter has wide bandwidth with slow slope unlike conventional narrow bandpass color filter. This enables distinction or multiple fluorescent colors with a single detector. The COST algorithm can differentiate 5 BV dyes using a single detector. FIG. 12D The schematic of SimpleFiex chip design with gold pin electrodes. The opening of sensing area is 30 μm and two gold pins are inserted to create narrowly confined electric field. FIG. 12E Beads with three different sizes are distinguished by measuring impedance signal from each bead. FIG. 12 The measurement over time shows the presence of three different sizes beads.

FIGS. 13A, 13B, 13C, 13D, 13E, 13F, and 13G show schematic diagrams and experimental data illustrating the detection of single stranded dengue synthetic RNA according to some embodiments of the invention. FIG. 13A Red band images on a lateral flow strip for different levels of the synthetic RNA, and FIG. 13B detection curve for synthetic RNA. FIG. 13C Detection of dengue virus form dengue patient plasma sample. FIG. 13D No detection of mismatch RNA template. A Probe is complementary to the match RNA and exhibits a single base mismatch with mismatch RNA. FIG. 13E Direct from blood detection of synthetic RNA spiked into healthy human blood. FIG. 13F Direct from nasopharyngeal samples detection of synthetic RNA spiked into healthy human nasopharyngeal biofluids. FIG. 13G A prototype of lateral flow assay for TARA according to some embodiments of the invention.

FIGS. 14A and 14B show schematic diagrams and experimental data where HRP attached to the GNP is used to achieve up to a 105 enhancement in signal according to some embodiments of the invention. FIG. 14A Without signal amplification. FIG. 14B Signal enhancement using the substrate TMB. The lateral flow assay is designed to detect specific reporter group-attached gold nanoparticles. Template Assisted Rapid Assay (TARA) using GNP-HRP double label yields 105 enhancement in signal according.

DETAILED DESCRIPTION OF THE PREFERRED EMBODIMENT

The present disclosure relates to, in one aspect, the direct detection and identification of nucleic acid sequences using Template Assisted Rapid Assay (TARA). In some embodiments, the TARA can be applied without sample preparations. Point of care may refer to, but not limited to, that clinicians deliver healthcare products and services to patients at the time and/or place of care. Point-of-care testing (POCT), or bedside testing may encompass, but not limited to, medical diagnostic testing at or near the point of care—that is, at the time and place of patient care. This can provide certain benefits over the historical pattern in which testing is substantially or partially confined to the medical laboratory, which may including sending off specimens away from the point of care and then waiting to learn the results. In some embodiments, the TARA can be applied in a (point of care) POC setting.

The present disclosure also relates to, in another aspect, the novel chemistry platform technology using Template Assisted Rapid Assay (TARA), PCR-free, rapid template-dependent transfer reaction assay directly from samples from, e.g. nasopharyngeal swab, nasal aspirate, oropharyngeal swab or blood. A transfer reaction employed in some embodiments is described in US 2011/0070577 A1, which is hereby incorporated in its entirety by reference.

Figure 4:
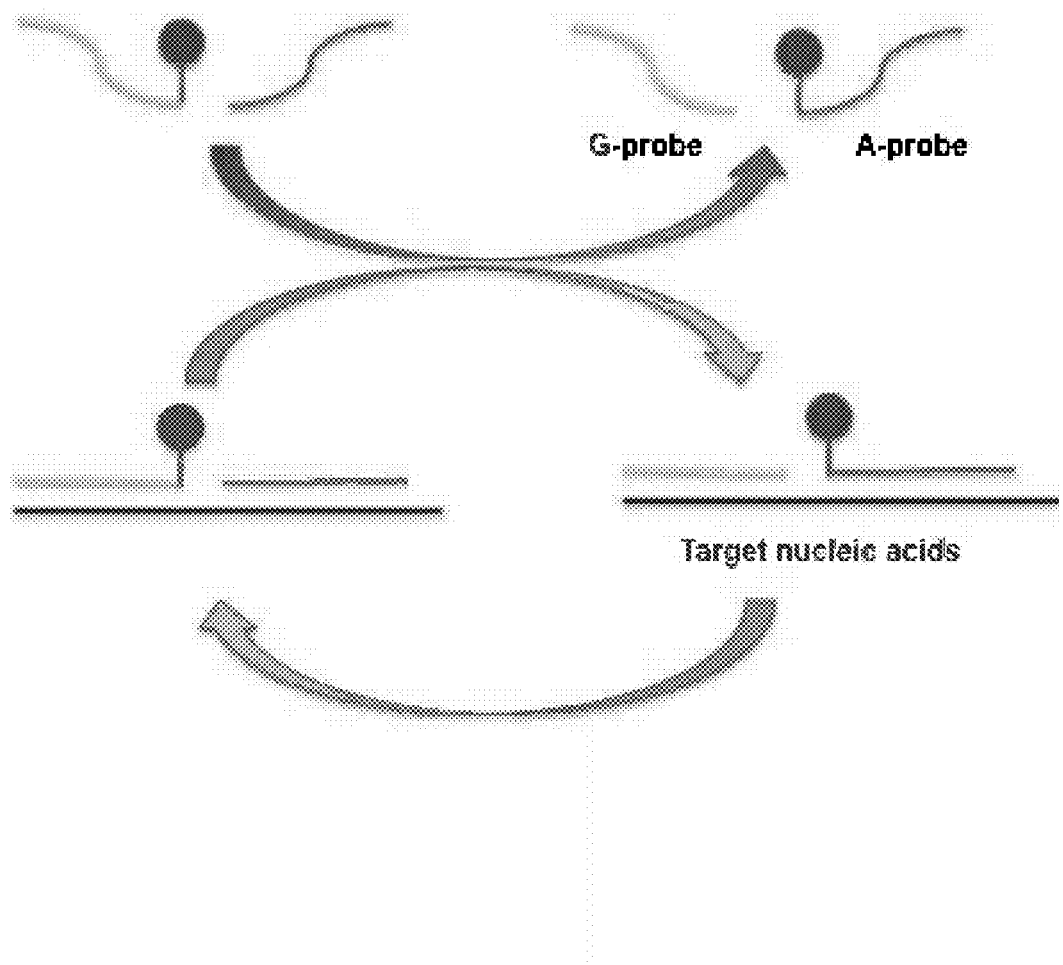
FIG. 4 shows schematic diagrams illustrating a general principle of TARA reactions according to some embodiments of the invention. G-probe is shown in yellow, A-probe is shown in orange, and target nucleic acids are shown as blue lines.

FIG. 4 provides a transfer reaction employed in some embodiments of the invention that can provide a method for detecting at least one target nucleic acid sequence in a sample. The methods in such embodiments may comprise the steps of:
(i) contacting the sample with at least one probe set for each target nucleic acid sequence, the probe set comprising:
(a) a probe 1 (or a first probe) comprising a first reporter group, which is capable of being transferred to a probe 2 (or a second probe), and a first nucleic acid region, which is complementary to a first part of the target nucleic acid sequence, and (b) a probe 2 comprising a second nucleic acid region, which is complementary to a second part of the target nucleic acid sequence and comprising a moiety which is capable of receiving said first reporter group when both probe 1 and probe 2 hybridize to the target nucleic acid, wherein said second part of the target nucleic acid sequence is substantially adjacent to the first part of the target nucleic acid;
(ii) exposing the sample to conditions which lead to the transfer of the first reporter group to the probe 2 when the target nucleic acid sequence is present; and
(iii) detecting probe 2 molecules to which said first reporter group has been transferred.

According to some embodiments, the probe set may comprise:
(a) a probe 1 having the structure (VI)

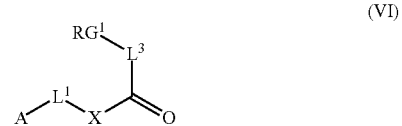

(VI)

X is S, O, Se, S—C(O), O—C(O), Se—C(O), or $P^+R^1R^2$, wherein the C(O) group, if present, is bound to $L^1$;
$R^1$ and $R^2$, if present, are independently selected from the group consisting of aryl and alkyl;
$L^1$ is a linker or a bond; $L^3$ is a linker or a bond;
A comprises a nucleic acid region, which is complementary to a first region of the target nucleic acid sequence, and optionally a second reporter group which is linked to said region via a covalent bond or a linker; and
(b) a probe 2 having the structure (VII) or (VIII)

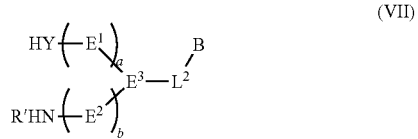

(VII)

wherein
E1 and E2 are independent of each other CHR", R" being a hydrogen, alkyl, alkenyl, alkynyl, cycloalkyl, heterocycloalkyl, aryl, heteroaryl, aralkyl, or a heteroaralkyl group;
E3 is selected from the group consisting of alkyl, alkenyl, heteroalkyl, and heteroalkenyl, cycloalkyl, heterocycloalkyl, alicyclic system, aryl or heteroaryl group; optionally substituted; and wherein E1 and E2 are attached to the same or to adjacent carbon and/or nitro-gen atom(s);
R' is hydrogen, an alkyl, alkenyl, alkynyl, cycloalkyl, heterocycloalkyl, aryl, heteroaryl, aralkyl, or a heteroaralkyl group;
Y is S, or Se;
L2 is a linker or a bond;
B comprises a nucleic acid region, which is complementary to a second region of the target nucleic acid sequence, and optionally a first reporter group which is linked to said region via a covalent bond or a linker; and one of a and b is 1 and the other one is 0 or both a and b are 1 or one of a and b is 2 and the other one is 0;
or VIII

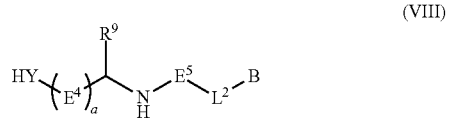

(VIII)

wherein
E4 in each instance is independently CHR", wherein R" is hydrogen, an alkyl, alkenyl, alkynyl, cycloalkyl, heterocycloalkyl, aryl, heteroaryl, aralkyl, or a heteroaralkyl group, optionally substituted;

E5 is CHR''' or CR''', wherein R''' is hydrogen, an alkyl, alkenyl, alkynyl, cycloalkyl, heterocycloalkyl, aryl, het R9 is hydrogen; alkyl; alkenyl; alkynyl; cycloalkyl; hetero-cycloalkyl; aryl; heteroaryl; aralkyl; or a heteroaralkyl group; optionally substituted or R9 and R''' are taken together to form a heterocycloalkyl, alicylic system or heteroaryl; optionally substituted;

Y is S, or Se;

L2 is a linker or a bond;

B comprises a nucleic acid region, which is complementary to a second region of the target nucleic acid sequence, and optionally a first reporter group which is linked to said region via a covalent bond or a linker; and a is 1 or 2;

wherein the second region of the target nucleic acid sequence is adjacent to the first region of the target nucleic acid.

According to some embodiments, the first reporter group is transferred from the first probe to the second probe by a chemical reaction selected from the group consisting of:

(a) substitution at the carbonyl carbon atom as depicted in reaction scheme (I):

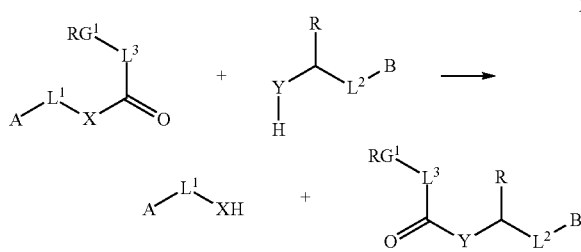

wherein $RG^1$ is a first reporter group;

X is S, O, Se, S—C(O), O—C(O), Se—C(O), or $P^+R^1R^2$, wherein the C(O) group, if present, is bound to $L^1$;

Y is NH, S, N—$R^4$, HN—O, $NR^4$—$NR^5$, O—O, O—NH, S—S, S—O, $PR^3$, $P(OR^3)$, Se, or a C nucleophile, wherein the S—O group is oriented in such that the O is bound to the carbon atom carrying the R group;

R is hydrogen, an alkyl, alkenyl, alkynyl, cycloalkyl, heterocycloalkyl, aryl, heteroaryl, aralkyl, or a heteroaralkyl group, optionally substituted;

$R^1$, $R^2$, and $R^3$, if present, are independently selected from the group consisting of aryl and alkyl;

$R^4$ and $R^5$, if present, are independently from each other hydrogen, an alkyl, alkenyl-, alkynyl, cycloalkyl, heterocycloalkyl, aryl, heteroaryl, aralkyl, or a heteroaralkyl group, optionally substituted;

$L^1$ is a linker or a bond; $L^2$ is a linker or a bond; $L^3$ is a linker or a bond;

A comprises a nucleic acid region, which is complementary to a first nucleic acid region of the target nucleic acid sequence, and optionally at least a second reporter group which is linked to said region via a covalent bond or a linker; and B comprises a nucleic acid region, which is complementary to a second nucleic acid region of the target nucleic acid sequence, and optionally at least a first reporter group which is linked to said region via a covalent bond or a linker;

(b) substitution at the alkyl carbon atom as depicted in reaction scheme (II):

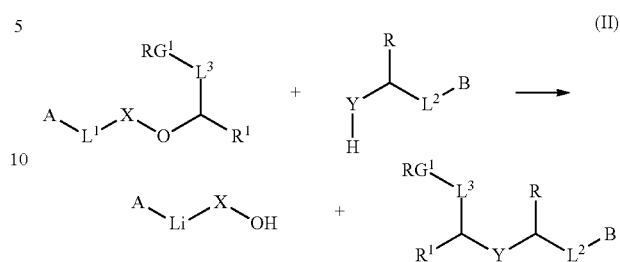

wherein $RG^1$ is a reporter group;

X is $SO^2$ or $P^+R^1R^2$;

Y is NH, S, S—PO, N—$R^5$, HN—O, $NR^5$—$NR^6$, O, O—O, ONH, S—S, S—O, $PR^4$, $P(OR^4)$, Se, Se—$PO^3$, S—O are oriented in such that the —$PO^3$ moiety or the O atom is bonded to the carbon atom carrying the R residue and S and Se are bonded to H before the reaction and to the carbon atom linked to $L^3$ after the reaction;

R is hydrogen, an alkyl, alkenyl, alkynyl, cycloalkyl, heterocycloalkyl, aryl, heteroaryl, aralkyl, or a heteroaralkyl group, optionally substituted;

$R^1$ is —CN, —$NO_2$, —COOAlk, —H, —CHO, —COAlk;

$R^2$, $R^3$, and $R^4$, if present, are independently from each other aryl and alkyl;

$R^5$ and $R^6$, if present, are independently from each other hydrogen, an alkyl, alkenyl, alkynyl, cycloalkyl, heterocycloalkyl, aryl, heteroaryl, aralkyl, or a heteroaralkyl group, optionally substituted;

$L^1$ is a linker or a bond; $L^2$ is a linker or a bond; $L^3$ is a linker or a bond;

A comprises a nucleic acid region, which is complementary to a first nucleic acid region of the target nucleic acid sequence, and optionally a second reporter group which is linked to said region via a covalent bond or a linker; and B comprises a nucleic acid region, which is complementary to a second nucleic acid region of the target nucleic acid sequence, and optionally a first reporter group which is linked to said region via a covalent bond or a linker;

(c) substitution at phosphate as depicted in reaction scheme (III):

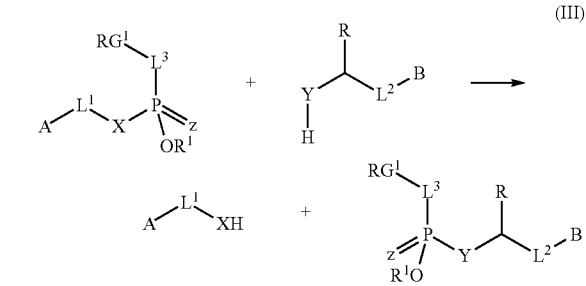

wherein $RG^1$ is a reporter group;

X is O, $NR^2$, or S;

Y is O, NH, Se or S;

Z is not present or O;

R and $R^1$ are independently from each other hydrogen, an alkyl, alkenyl, alkynyl, cycloalkyl, heterocycloalkyl, aryl, heteroaryl, aralkyl, or a heteroaralkyl group, optionally substituted;

$R^2$, if present, is hydrogen, an alkyl, alkenyl, alkynyl, cycloalkyl, heterocycloalkyl, aryl, heteroaryl, aralkyl, or a heteroaralkyl group, optionally substituted;

$L^1$ is a linker or a bond; $L^2$ is a linker or a bond; $L^3$ is a linker or a bond;

A comprises a nucleic acid region, which is complementary to a first nucleic acid region of the target nucleic acid sequence, and optionally a second reporter group which is linked to said region via a covalent bond or a linker; and B comprises a nucleic acid region, which is complementary to a second nucleic acid region of the target nucleic acid sequence, and optionally a first reporter group which is linked to said region via a covalent bond or a linker;

(d) Staudinger reaction as depicted in reaction scheme (IV):

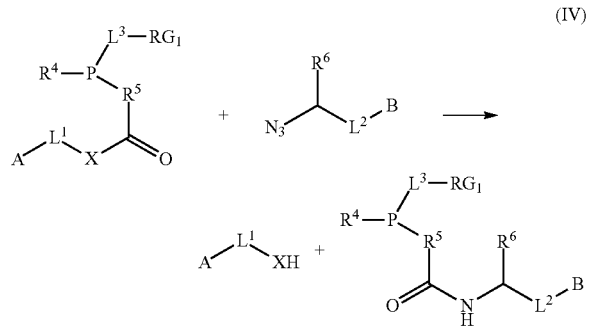

(IV)

wherein $RG_1$ is a reporter group;

X is O, S, Se, or $NR^3$, wherein $R^3$ is H or alkyl;

$R^4$ is hydrogen, an alkyl, alkenyl, alkynyl, cycloalkyl, heterocycloalkyl, aryl, heteroaryl, aralkyl, or a heteroaralkyl group, optionally substituted;

$R^5$ is an alkyl, alkenyl, alkynyl, cycloalkyl, heterocycloalkyl, aryl, heteroaryl, aralkyl, or a heteroaralkyl group, optionally substituted;

$R^6$ is hydrogen, an alkyl, alkenyl, alkynyl, cycloalkyl, heterocycloalkyl, aryl, heteroaryl, aralkyl, or a heteroaralkyl group, optionally substituted;

$L^1$ is a linker or a bond; $L^2$ is a linker or a bond; $L^3$ is a linker or a bond;

A comprises a nucleic acid region, which is complementary to a first nucleic acid region of the target nucleic acid sequence, and optionally a second reporter group which is linked to said region via a covalent bond or a linker; and B comprises a nucleic acid region, which is complementary to a second nucleic acid region of the target nucleic acid sequence, and optionally a first reporter group which is linked to said region via a covalent bond or a linker;

(e) Wittig reaction as depicted in reaction scheme (V):

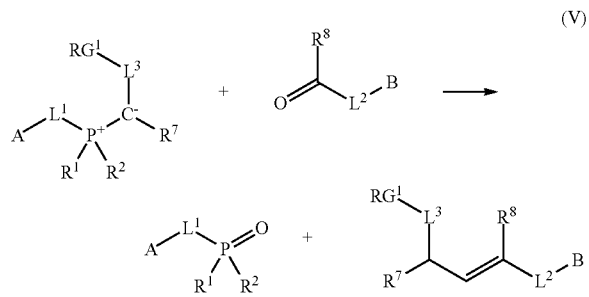

(V)

wherein $RG^1$ is a reporter group;

$R^1$ and $R^2$ are independently from each other selected from the group consisting of hydrogen, an alkyl, alkenyl, alkynyl, cycloalkyl, heterocycloalkyl, heteroaryl, aralkyl, and a heteroaralkyl group, optionally substituted;

$R^7$ is C(O)N-alkyl, $NO_2$, CN, C(O)-alkyl, C(O)O-alkyl, aryl, heteroaryl, fluorinated alkyl;

$R^5$ is hydrogen, $CH=CH_2$, aryl, alkyl;

$L^1$ is a linker or a bond; $L^2$ is a linker or a bond; $L^3$ is a linker or a bond;

A comprises a nucleic acid region, which is complementary to a first nucleic acid region of the target nucleic acid sequence, and optionally a second reporter group which is linked to said region via a covalent bond or a linker; and B comprises a nucleic acid region, which is complementary to a second nucleic acid region of the target nucleic acid sequence, and optionally a first reporter group which is linked to said region via a covalent bond or a linker.

In certain embodiments, the one or more linkers from the above compounds are selected from the group consisting of an alkyl, alkenyl, alkynyl, cycloalkyl, heterocycloalkyl, aryl, heteroaryl, aralkyl, and a heteroaralkyl group, optionally substituted.

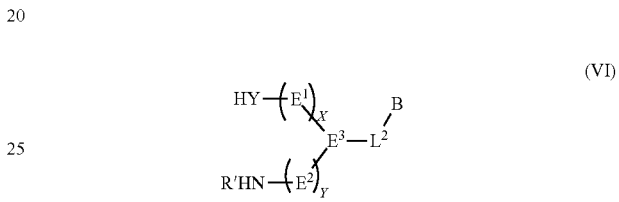

(VI)

wherein $E^1$ and $E^2$ are independent of each other CHR", wherein R" is hydrogen, alkyl, alkenyl, alkynyl, cycloalkyl, heterocycloalkyl, aryl, heteroaryl, aralkyl, or a heteroaralkyl group;

$E^3$ is selected from the group consisting of alkyl, alkenyl, heteroalkyl, and heteroalkenyl, cycloalkyl, heterocycloalkyl, alicyclic system, aryl or heteroaryl group; optionally substituted; and wherein $E^1$ and $E^2$ are attached to the same or to adjacent carbon and/or nitrogen atom(s);

R' is hydrogen, an alkyl, alkenyl, alkynyl, cycloalkyl, heterocycloalkyl, aryl, heteroaryl, aralkyl, or a heteroaralkyl group;

$L^2$ is a linker or a bond;

B comprises a nucleic acid region, which is complementary to a second nucleic acid region of the target nucleic acid sequence, and optionally a first reporter group which is linked to said region via a covalent bond or a linker;

Y is S or Se; and one of X and Y is 1 and the other one is 0 or both X and Y are 1 or one of X and Y is 2 and the other one is O;

or formula (VII):

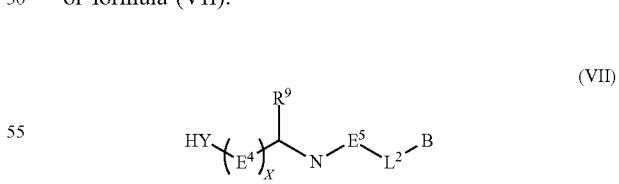

(VII)

wherein $E^4$ in each instance is independently CHR", wherein R" is hydrogen, an alkyl, alkenyl, alkynyl, cycloalkyl, heterocycloalkyl, aryl, heteroaryl, aralkyl, or a heteroaralkyl group, optionally substituted;

$E^5$ is CHR'" or CR'", wherein R'" is hydrogen, an alkyl, alkenyl, alkynyl, cycloalkyl, heterocycloalkyl, aryl, heteroaryl, aralkyl, or a heteroaralkyl group, optionally substituted;

R⁹ is hydrogen; alkyl; alkenyl; alkynyl; cycloalkyl; hetero-cycloalkyl; aryl; heteroaryl; aralkyl; or a heteroaralkyl group; optionally substituted or R9 and R''' are taken together to form a heterocycloalkyl, alicylic system or heteroaryl; optionally substituted;

$L^2$ is a linker or a bond;

B comprises a nucleic acid region, which is complementary to a second nucleic acid region of the target nucleic acid sequence, and optionally a first reporter group which is linked to said region via a covalent bond or a linker; and Y is S or Se; and x is 1 or 2.

In some embodiments, the distance between the first part and the second part of the target nucleic acid sequence, the distance between the first part and the third part of the target nucleic acid sequence, and/or the distance between the second part and the third part of the target nucleic acid sequence is substantially adjacent. In some embodiments, the distance between two different probes may be 0, 1, 2, 3, 4, 5, 6, 7, 8, 9, to 10 nucleotides. In some other embodiments, the distance between the two different probes may be more than 10 nucleotides. In some other embodiments, the distance between the two different probes is substantially adjacent which can range from 0 to 100 nucleotides, 0-50 nucleotides, 0-40 nucleotides, 0-30 nucleotides, 0-20 nucleotides, 0-10 nucleotides, 0-5 nucleotides, 0-4 nucleotides, 0-3 nucleotides, 0-2 nucleotides, or 0-1 nucleotides. In some other embodiments, the distance between the two different probes is 0 nucleotide such that the two probes are immediately adjacent to each other when they hybridize to the target nucleic acid.

In some embodiments, the target nucleic acid sequence is not limited in size such that the target nucleic acid sequence can comprise at least two nucleic acids and more. In some embodiments, the target nucleic acid may comprise about five, about ten, about fifteen, about twenty, about thirty, about forty, about fifty, about sixty, about seventy, about eighty, about ninety, about hundred, about several hundreds, about thousand, about several thousands, or any intervening number of the foregoing of nucleic acids.

TARA may utilize, at least in some embodiments, RNA (DNA)-assisted antibody (or biotin) transfer on nano- or micro-sized particles. This nano- or micro-technology is used to multiplex detect and identify nucleic acid sequences without the necessity of using enzymatic nucleic acid amplification methods. In certain embodiments, TARA reaction utilizes a magnetic gold-nanoparticle(s). In some embodiments, probe 2 comprise one or more nano- or micro-sized particles that are capable of carrying a plurality of the second nucleic acid region which is complementary to the second part of the target nucleic acid sequence. Therefore, in certain embodiments, each of the nano- or micro-sized particles presents a plurality of the second nucleic acid region that is ligated with the first nucleic acid region of probe 1 in a template-dependent manner, resulting in transferring the first reporter group from probe 1 to probe 2. Given the presence of numerous copies of the second nucleic acid region in individual nano- or micro-sized particles of probe 2, the density of the first reporter group recruited to probe 2 (or the intensity of the signal generated from the first reporter group recruited to probe 2), through the transfer reaction, becomes substantially increased. This results in significant enhancement of the sensitivity of the assay. With this mechanism, the TARA reaction according to some embodiments of the invention allows the sensitive and reliable detection of the presence and/or level of a target nucleic acid sequence, without necessarily extracting and amplifying the target nucleic acid sequence. Optionally, in certain embodiments of the invention, there can be further enrichment of a plurality of probe 2 that comprises the first reporter group transferred from probe 1 such that the sensitivity and accuracy of the assay becomes even further improved to the extent that the extraction and/or amplification of the target nucleic acid sequence is not needed. Due to the foregoing mechanisms allowing the high sensitivity and reproducibility, the method based on TARA reactions in certain embodiments of the present invention allows rapid and substantially instant detection of the target nucleic acid sequence in a sample which makes it particularly suitable for the point of care (POC) application. Methods, reagents, and kits for detecting, identifying and quantifying nucleic acid sequences for pathogen detections can utilize the foregoing system.

In certain embodiments, one or more nano- or micro-particles comprises one or more probes. In some of such embodiments, one or more probes can be associated, via, e.g. a covalently and/or non-covalently bond, with one or more nano- or micro-particles. Therefore, when the nano- or micro-particles are collected or isolated, it may result in purification of the probes attached/associated with the nano- or micro-particles particles. Such collection or isolation of the nano- or micro-particles may comprise one or more of, e.g. permanent or temporary immobilization, retainment, or stabilization of the nano- or micro-particles on a medium, and alliteratively collecting or harvesting the nano- or micro-particles such that the nano- or micro-particles become partially or substantially isolated from the rest of the reaction mixture. Therefore, the probes associated with the nano- or micro-particles can also be collected or isolated.

As mentioned above, TARA reactions may utilize nano- or micro-sized particles, especially for the purpose of carrying a second nucleic acid region that is complementary to the second part of the target nucleic acid sequence. The nano- or micro-sized particles may be selected from the group consisting of gold nanoparticle, silver nanoparticle, microbead, and any mixture thereof. In certain embodiments, the nano-sized particles may comprise particles between about 1 nm to 100 nm in size. In some other embodiments, the nano-sized particles may comprise particles between about 100 nm to 1000 nm in size, and in some alternative embodiments, the size can be more than about 1000 nm. The micro-sized particles, which can be made with any types of metals, or synthetic or natural plastic materials, can range between about 1 μm and about 100 μm in size according to some embodiments. In some other embodiments, the size of the micro-sized particles can be between about 100 μm and about 1000 μm, and in some other alternative embodiments, the size of the micro-sized particles can be more than about 1000 μm.

According to one aspect, the nano- or micro-sized particles can carry a plurality of second nucleic acid region that is complementary to the second part of the target nucleic acid sequence. An average number of the second nucleic acid region present on each of the nano- or micro-sized particles may vary from at least two to more. In some embodiments, the average number of the second nucleic acid region present on each of the nano- or micro-sized particles may be about 10, about 50, about 100, about 150, about 200, about 250, about 300, about 350, about 400, about 450, about 500, about 102, about 103, about 104, about 105, about 106, and about 107 or any intervening number of the foregoing.

The practice of some embodiments can employ conventional techniques and descriptions of organic chemistry, polymer technology, molecular biology (including recombinant techniques), cell biology, biochemistry, and immunology, which are within the skill of the art. Such techniques may include polymer array synthesis, hybridization, ligation, and detection of hybridization using a label. Specific illustrations of suitable techniques can be had by reference to the example herein below. However, other equivalent conventional procedures can also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5'" Ed, W. H. Freeman Pub., New York, N.Y., all of which are hereby incorporated in their entirety by reference for all purposes. Furthermore, all references cited in this application are herein incorporated in their entirety by reference for all purposes.

1. Principles of TARA Technologies

A general problem of the template mediated ligation reaction that prevents signal amplification is product inhibition. Product inhibition is the blockage of the template by the reaction product. In the case of ligation reactions, product inhibition is due to entropic reasons.

Figure 1:
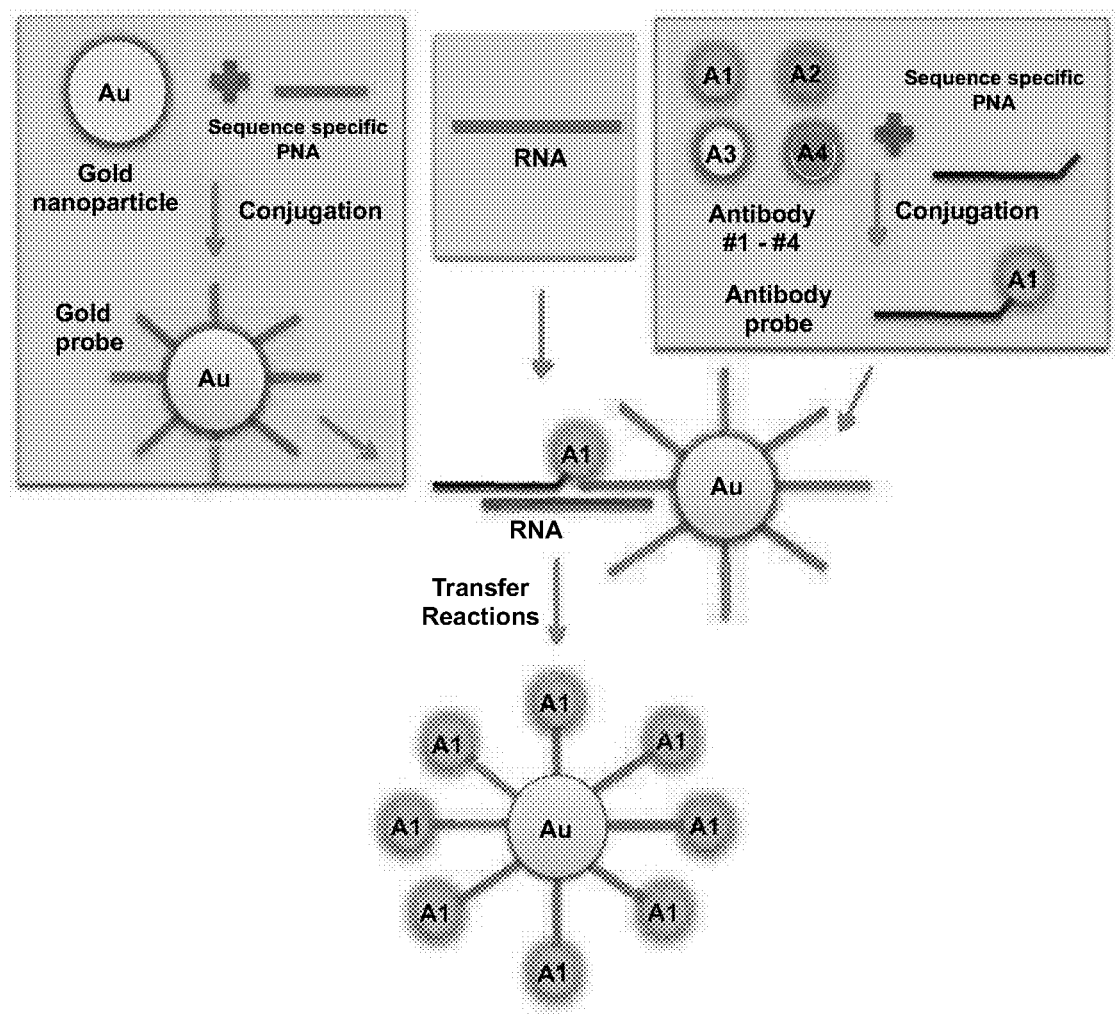
FIG. 1 shows schematic diagrams illustrating the Template Assisted Rapid Assay (TARA) which comprises RNA-assisted antibody transfer on gold nanoparticles according to some embodiments of the invention.
Figure 2:
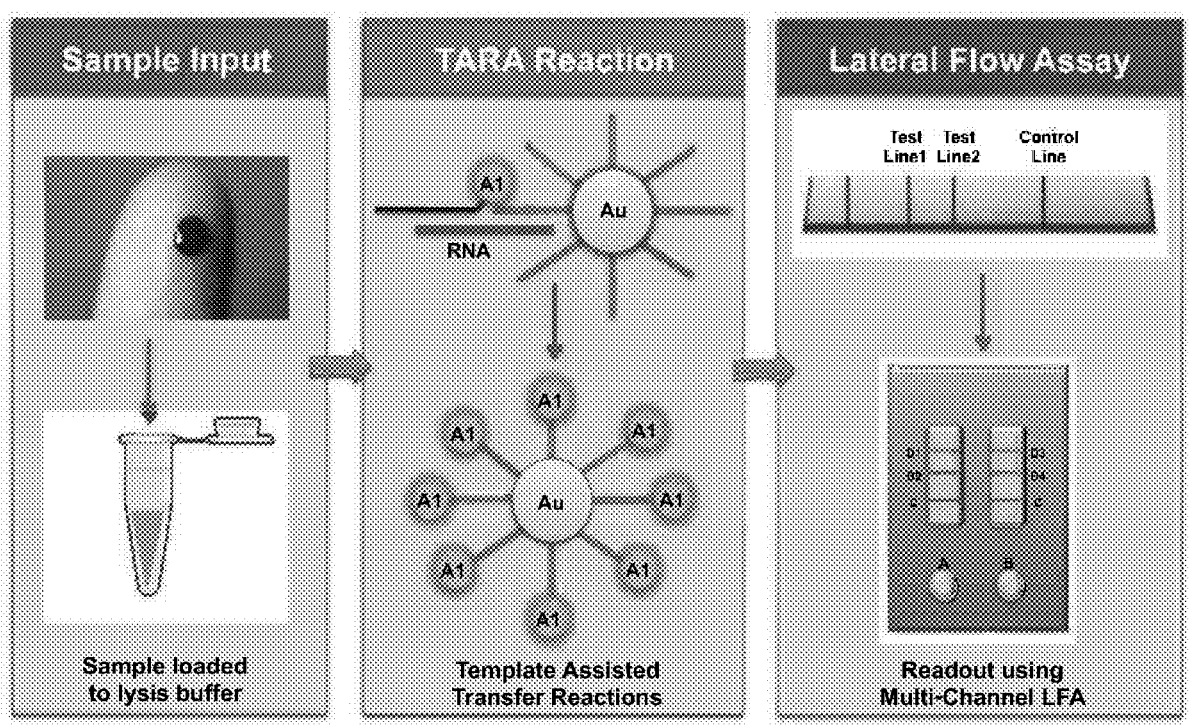
FIG. 2 shows another schematic diagrams showing the TARA (Template Assisted Rapid Assay) Technology platform, in particular, where a sample is obtained from a subject's blood according to some embodiments of the invention.
Figure 3:
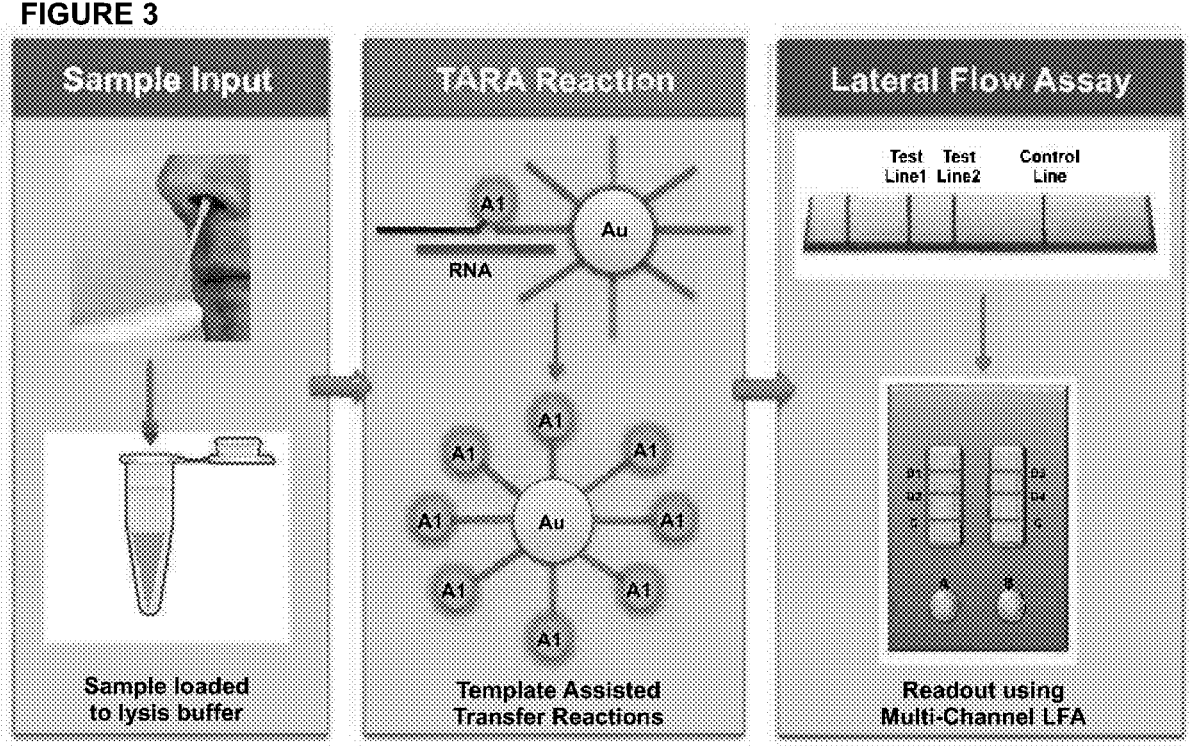
FIG. 3 shows another schematic diagrams showing the TARA (Template Assisted Rapid Assay) Technology platform, in particular, where a sample is obtained from nasopharyngeal swab, nasal aspirate, or oropharyngeal swab from a subject according to some embodiments of the invention.

Both molecular and product signal amplification are desired when the target nucleic acid (DNA or RNA) is present at low concentration. An increased affinity of the product to the target nucleic acid from template-controlled chemical ligation reactions suffers from product inhibition and prevents high catalytic activity of the nucleic-acid template. A reaction is used in which the target nucleic acid serves as a catalyst involving a transfer reaction, in which a reporter group (Q) is transferred from one probe to second probe by a native chemical ligation-like mechanism. Nucleic acid-assisted antibody transfer on a gold nanoparticle representing certain embodiments is shown in FIG. 1. The TARA (Template Assisted Rapid Assay) Technology platform according to various embodiments is shown in FIG. 2 (a direct assay from blood sample) and FIG. 3 (a direct assay from nasopharyngeal swab, nasal aspirate, or oropharyngeal swab samples), respectively.

2. TARA Chemistry

Figure 5:
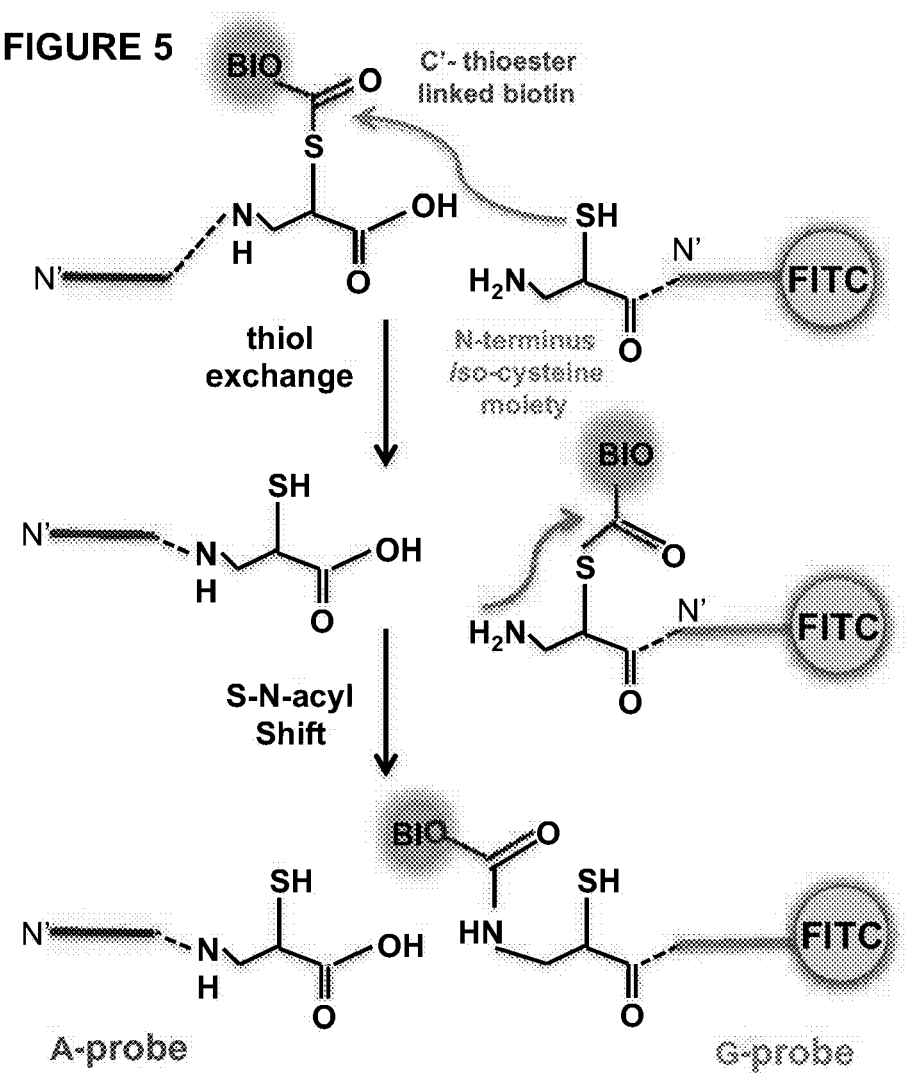
FIG. 5 shows another schematic diagrams illustrating a principle of TARA reactions according to some embodiments of the invention. In this particular embodiment, transfer of an antibody is done by a native chemical ligation-like reaction. The reporter group (antibody or biotin) is first transferred to a thiol group of the acceptor G-probe (gold nanoparticle-linked PNA probe), and then in an irreversible intramolecular reaction to an amino group of the acceptor G-probe.

The DNA/RNA acts as a catalyst in a transfer reaction, which proceeds via a native chemical ligation-like mechanism. See FIG. 1 which describes two probe system. For example, DNA/RNA-triggered acyl transfer can be used to transfer a thioester-linked dabcyl reporter group (dark red, FIG. 4) from the donor conjugate to the acceptor probe, which bears an n-terminal iCyl capable of attacking the thioester in a native chemical ligation-like fashion (FIG. 5). This reaction scheme allows for 400 turnovers at $10^4$-fold excess and relatively low concentration (100 nm) of reactant probes and has been applied to the transfer of biotin. The reaction combines a high catalytic activity of the target DNA with useful yields and low background (3.4% non-templated transfer after 24 h). Alternatively, a template-controlled aminolysis reaction that allows high catalytic turnover numbers or PNA conjugates by RNA programmed peptidyl transfer can be used.

In one embodiment, using a transfer reaction chemistry, gold nanoparticle probes and a paper strip or a microfluidic device, The Template Assisted Rapid Assay (TARA) is used for POC-rapid detection of, for example, dengue virus directly from whole blood samples. See FIGS. 1 and 2. The multiplex POC dengue detection test is fast and based on a disposable paper strip or a microfluidic device, providing a nucleic acid POC diagnostic device capable of detection of dengue virus as well as identification of four serotypes of dengue virus with high sensitivity and specificity. Unlike its RT-PCR equivalent, the TARA reaction can directly target the RNA of interest, eliminating the need of RNA isolation and cDNA production. Furthermore, the TARA reaction is notably tolerant of sample impurities and works just as well in the presence of RNA stabilization reagents as with highly purified RNA. As a result, it can be used directly to analyze stabilized RNA in whole blood and tissue (FIG. 2).

A simple assay for multiplex detections of target regions based on the TARA system is presented. This includes, in some embodiments, the development of multiplex dengue diagnosis assay, influenza virus, chikungunya virus, and malaria using an innovative RNA chemistry TARA.

In some embodiments, the target nucleic acid sequence is associated with one or more selected from the group consisting of dengue virus, influenza virus, chikungunya virus, the human immunodeficiency virus (HIV), the Hepatitis C virus (HCV), Human papillomavirus (HPV), Middle East Respiratory Syndrome (MERS) virus, arboviruses, and methicillin-resistant staphylococcus aureus (MRSA).

In some other embodiments, the target nucleic acid sequence is associated with one or more selected from the group consisting of a bacterium, a fungus and a parasite.

In still some other embodiments, the target nucleic acid sequence is associated with nucleic acid biomarkers selected from the group consisting of RNA, DNA, and microRNA in non-communicable and/or chronic diseases.

Template Assisted Rapid Assay (TARA) according to some embodiments of the present invention exhibits at least the following feature: (i) the reaction is fast enough to allow a real-time detection of nucleic acids, (ii) the transfer of a reporter group allows differentiating between the specific template-mediated reaction and unspecific background hydrolysis, (iii) the reaction is not significantly impaired by product inhibition, thus enabling the detection of substoichiometric amounts of target nucleic acids, iv) extensive sample preparation such as RNA or DNA extraction is not required, v) PCR is not required, vi) isothermal amplification is not required, and vii) instrumentation is not required.

In some embodiments, methods for detecting at least one target nucleic acid sequence in a sample are provided. In certain embodiments, the method may comprise the steps of: contacting the sample with at least one probe set for each target nucleic acid sequence. The probe set may comprise (a) a plurality of probe 1, probe 1 comprising a first reporter which is capable of being transferred to probe 2, and a first nucleic acid region, said first nucleic acid region being complementary to a first part of the target nucleic acid sequence, and (b) a plurality of probe 2, probe 2 comprising a second nucleic acid region complementary to a second, different part of the target nucleic acid sequence, said first part and said second part of the target nucleic acid sequence being substantially adjacent to each other in the target nucleic acid sequence. The plurality of probe 2 may be associated with one or more nano- or micro-particles. In the presence of the target nucleic acid sequence, the first reporter group in probe 1 may be transferred to probe 2. The method may also comprise measuring the presence and/or level of the first reporter group that has been transferred to probe 2. The target nucleic acid sequence may not be amplified prior to contacting the sample with mixture.

In a further aspect a kit is provided for detecting at least one target nucleic acid sequence in a sample comprising one probe set for each target nucleic acid sequence, the probe set comprising:

(a) a probe 1 having the structure (VIII)

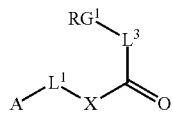
(VIII)

RG1 is a first reporter group;

X is S, O, Se, S—C(O), O—C(O), Se—C(O), or P$^+$R$^1$R$^2$, wherein the C(O) group, if present, is bound to L$^1$; R$^1$ and R$^2$, if present, are independently selected from the group consisting of aryl and alkyl;

L$^1$ is a linker or a bond;

L$^3$ is a linker or a bond;

A comprises a nucleic acid region, which is complementary to a first nucleic acid region of the target nucleic acid sequence, and optionally a second reporter group which is linked to said region via a covalent bond or a linker; and (b) a probe 2 having the structure (VI)

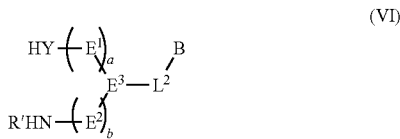
(VI)

wherein E$^1$ and E$^2$ are independent of each other CHR", R" being a hydrogen, alkyl, alkenyl, alkynyl, cycloalkyl, heterocycloalkyl, aryl, heteroaryl, aralkyl, or a heteroaralkyl group, optionally substituted;

E$^3$ is selected from the group consisting of alkyl, alkenyl, heteroalkyl, and heteroalkenyl, cycloalkyl, heterocycloalkyl, alicyclic system, aryl or heteroaryl group; optionally substituted; and wherein E$^1$ and E$^2$ are attached to the same or to adjacent carbon and/or nitrogen atom(s), optionally substituted;

R' is hydrogen, an alkyl, alkenyl, alkynyl, cycloalkyl, heterocycloalkyl, aryl, heteroaryl, aralkyl, or a heteroaralkyl group;

Y is S or Se;

L2 is a linker or a bond;

B comprises a nucleic acid region, which is complementary to a second nucleic acid region of the target nucleic acid sequence, and optionally a first reporter group which is linked to said region via a covalent bond or a linker; and one of a and b is 1 and the other one is 0 or both a and b are 1 or one of a and b is 2 and the other one is 0;

or the structure (VII)

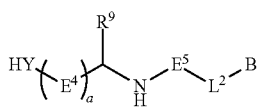
(VII)

wherein E$^4$ in each instance is independently CHR", wherein R" is hydrogen, an alkyl, alkenyl, alkynyl, cycloalkyl, heterocycloalkyl, aryl, heteroaryl, aralkyl, or a heteroaralkyl group, optionally substituted;

E$^5$ is CHR'" or CR'", wherein R'" is hydrogen, an alkyl, alkenyl, alkynyl, cycloalkyl, heterocycloalkyl, aryl, heteroaryl, aralkyl, or a heteroaralkyl group, optionally substituted;

R$^9$ is hydrogen; alkyl; alkenyl; alkynyl; cycloalkyl; heterocycloalkyl; aryl; heteroaryl; aralkyl; or a heteroaralkyl group; optionally substituted or R$^9$ and R'" are taken together to form a heterocycloalkyl, alicylic system, or heteroaryl, optionally substituted;

Y is S or Se;

L$^2$ is a linker or a bond;

B comprises a nucleic acid region, which is complementary to a second nucleic acid region of the target nucleic acid sequence, and optionally a first reporter group which is linked to said region via a covalent bond or a linker; and a is 1 or 2.

In a further aspect, the methods and kits can be for determining the sequence of a target nucleic acid, for the detection of at least one single nucleotide polymorphism in at least one target nucleic acid, and for the detection of at least one target nucleic acid from at least one pathogenic or allergenic organism.

In some embodiments, three different template-assisted chemical transfer chemistries can be used to maximize product turnover and signal-amplification reproducibility. Amplification of product signals is desired when the DNA or RNA is present at low concentration. In certain embodiments, three or more probes can be used in the TARA reactions. Two RNA-triggered reactions [acyl-transfer and Wittig reaction] are described that may allow intracellular applications and "PCR-less" RNA-detection. RNA-triggered acyl transfer which can be used to transfer a thioester-linked dabcyl reporter group (FIG. 4) from the donor conjugate to the acceptor probe, which bears an n-terminal iCyl capable of attacking the thioester in a native chemical ligation-like fashion. Alternatively, a template-controlled aminolysis reaction that allows high catalytic turnover numbers [12-15] or PNA conjugates by RNA programmed peptidyl transfer can be used. A wittig reaction that leads to transfer of a benzylidene group from a DNA-linked phosphonium salt to a DNA-linked benzaldehyde may be used. The reaction yield, turnover and reaction rates for at least 5 synthetic RNA target are determined and the ability to simultaneously determine their relative concentrations demonstrated. The rate of reaction is not the only variable of importance for the optimization of RNA-triggered transfer reaction, but also the removal of product inhibition following transfer reactions. In order to achieve significant turnover, the chemical transfer product must be less stable (lower Tm) than the un-transferred probes and be disassociated from the target following reaction. For example, while the PNA probes described above display extremely fast reaction rates, they do not generate significant amounts of product turnover, presumably due to slow disassociation of the transferred product.

Since the RNA-triggered transfer reaction does not require RNA purification and cDNA synthesis at least in some embodiments, a sample stabilized in a simple stabilization buffer from a viral RNA sample preparation kit may be used directly. By eliminating the need for RNA purification, RNA characterization and cDNA synthesis, this assay method dramatically shortens the result turn-around time and eliminates major sources of assay imprecision. In addition, the stabilization buffer allows direct analysis of blood RNA without RNA purification or isolation (FIG. 2).

Blood sample preparation using self-administered Fingerstick disposable lancet from Roche Inc. is valid for use with TARA. Following a Lancet™ stick, two drops of blood (approximately 200 µl) are transferred to the tube containing a simple stabilization buffer (FIG. 2). The method may comprise the following: 1. Fingerstick blood collection; 2. blood into the tube; 3. Lyse cells and add RNA-triggered transfer reaction reagent thereto; and 4. Read result.

3. TARA Chemistry Directly From Blood Samples

According to some embodiments, target specific nucleic acid, e.g. PNA probes to gold nanoparticles and antibody can be prepared. Each G-probe may contain a 3'-biotin, a target hybridization sequence, and a 5' a cysteine moiety (FIG. 5). Each A-probe may contain a 3'-thioester-link, and biotin that can be conjugated with an antibody, and a target hybridization sequence (FIG. 5). S-HyNic and S-4FB (Solulink) can be used for conjugation of streptavidin to specific antibody according to the manufacturer's protocols from Solulink Inc. Streptavidin-conjugated nanoparticles are attached to the 3' end of A-probes and Streptavidin-antibody is conjugated to the 3' end of A-probes at room temperature for 60 minutes. The reaction system involves two reactive oligonucleotide probes. A 3'-thiolated PNA (A probe) serves as a donor probe and is armed with a thioester-linked antibody (FIG. 5). The acceptor PNA (G probe) is equipped with a cysteine moiety at the 5'-end and a biotin at the 3'-terminus. The transfer reaction proceeds only in the presence of complementary templates of viral RNA. FIG. 5 shows the principle of template assisted transfer reactions according to certain embodiments. Transfer of an antibody can be done by a native chemical ligation-like reaction (FIGS. 1 and 5). The reporter group (e.g. antibody or biotin) is first transferred to a thiol group of the acceptor G-probe (gold nanoparticle-linked PNA probe), and then in an irreversible intramolecular reaction to an amino group of the acceptor G-probe (FIGS. 1 and 5).

The target specific PNA probes with nanoparticles can detect unamplified nucleic acids. A technique is developed for an "RNA-assisted antibody transfer on a magnetic gold-nanoparticle" that uses nanotechnology to detect and identify RNA sequences in a multiplexed manner without the necessity of using enzymatic molecular amplification methods. The technique can be used for immobilization of the acceptor G-probe onto the surface of a streptavidin-modified gold-nanoparticle. In the presence of a complementary nucleic acid template, the nanoparticle-bound acceptor G-probe recruits the antibody-bound donor A-probe (FIGS. 1 and 5). The G-probe and A-probe hybridizing sequences are designed to be complementary to substantially adjacent sequences in a target nucleic acid sequence.

In one embodiment where the detection of dengue virus is concerned, the dengue viral RNA may capture two probes, e.g. A-probe and G-probe. When the two probes hybridize to the target, i.e. part of the dengue viral RNA, the proximity of the probes triggers an acyl transfer reaction between G-probe and A-probe, e.g. the transfer of the thioester linked antibody, which is used as a reporter group, from the donor A-probe to the acceptor G-probe. Therefore, Watson-Crick base-pairing is utilized to bring both reagents in the proximity close enough to react, thus significantly increasing their effective molarity and the transfer of a reporter group (e.g. antibody or biotin) by a native chemical ligation-like mechanism. The template-assisted acyl transfer reaction can be optimized (FIGS. 1, 4 and 5) between G-probe and A-probe at various loads of template RNA (Conditions: 5 nM Probe, 100 nM 1, 200 nM 2, 100 mM NaCl, 10 mM $NaH_2PO_4$, 2 mM TCEP, pH 7.4, 30° C.). Multiplexed probe sets can be used for the detection of dengue viral RNA in some embodiments. The feasibility for quick sample preparation was tested using magnetic gold-nanoparticle probes (FIG. 5) and the yield was quantitatively assessed using Nanodrop and RNA quality using Bioanalyzer.

According to certain embodiments, a disposable, nucleic acid-based test utilizing magnetic gold nanoparticle probes is provided as a lateral flow strip or a microfluidic device. A Point-of-Care (POC) assay on a paper dipstick or a microfluidic device can be used to identify dengue virus (or other target nucleic acids) without using enzymatic amplification methods. The technical feasibility for immobilization of the specific antibody onto the lateral flow strip is depicted in an illustrative and non-limiting embodiment shown in FIG. 6. For the lateral flow design and the lateral flow assay development, the general antigen/antibody interactions pairs (protein A/mouse IgG, protein A/human IgG), and antibody/secondary antibody interactions pairs (mouse IgG/goat-anti-mouse IgG, human IgG/goat-anti-human IgG) can be used. For Lateral Flow Assay (LFA) development, the LFA can quantitatively detect antibody-linked gold-nanoparticles (goat-anti-mouse IgG and goat-anti-human IgG) from viral RNA-assisted TARA reaction used as for dengue virus. Mouse and human IgG is conjugated on the detection pad to interact secondary antibodies (goat-anti-mouse IgG, goat-anti-human IgG). Protein A that interacts both mouse and human IgG is conjugated on the control lane (FIG. 6). The number of antibody-linked gold nanoparticles captured in the detection zone (antigen) would be comparable to the number of viral RNA copies dispensed onto the strips, providing a quantitative detection modality (FIG. 6).

Experimental condition to consider for successful LFA may include, but not limited to: 1) Capture PNA concentration, 2) Type of running buffer, 3) Nitrocellulose flow rate, 4) Gold nanoparticle size, 5) Gold nanoparticle orientation, 6) Ionic strength of wash and running buffer, 7) Time to incubate GNP probes and RNA target, 8) Lateral flow strip width, and 9) Temperature. Basically, antibody-linked gold nanoparticles react with its complimentary antigenic determinant to produce a visual reaction as a read-out on a paper dipstick (FIGS. 5 and 6).

Figure 7:
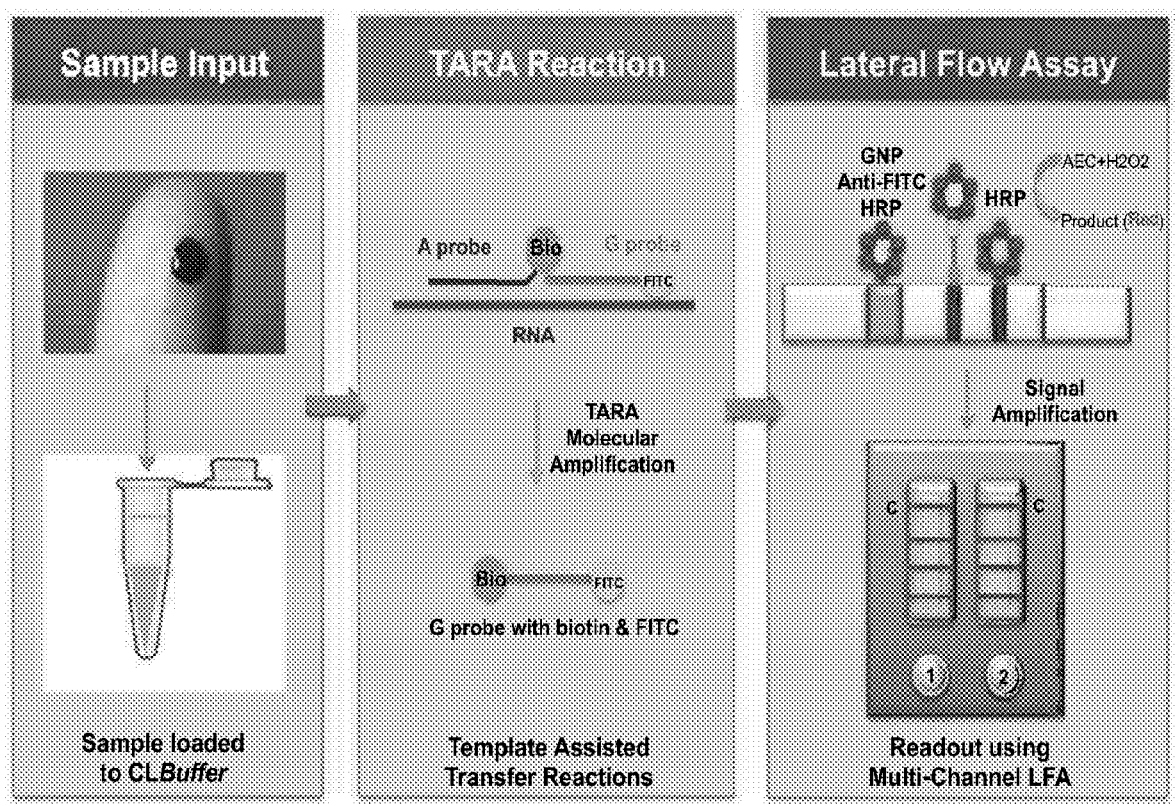
FIG. 7 shows another schematic diagrams illustrating TARA (Template Assisted Rapid Assay) Technology platform. In some embodiments, TARA uses chemical transfer reaction for molecular amplification, gold nanoparticle (GNP) and HRP for signal amplification, and the lateral flow assay for rapid, sensitive, and reproducible technique that will be used to develop POC diagnostic tools. In the embodiment illustrated in this figure, a sample such as a subject's blood is collected and provided into a tube where the cells are lysed and RNA-triggered transfer reaction reagents are added. The reporter group (blue circle) is transferred from the A probe to the G probe in a template-dependent manner. The reaction mix is then added to a paper strip or microfluidic device and the GNP-HRP-anti-FITC are conjugated to the FITC group on the G-probe on the conjugation pad. The reporter group labelled G probe is retained on the test line by a streptavidin or antibody, and the colorimetric signals are detected visually according to some embodiments of the invention.
Figure 9A:
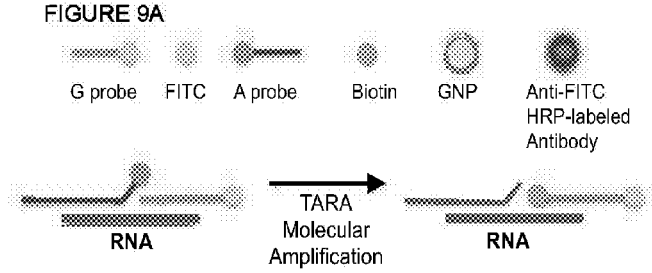
FIGS. 9A, 9B, 9C and 9D show schematic diagrams illustrating Template Assisted Rapid Assay (TARA) using GNP-HRP double label according to some embodiments of the invention.
Figure 9B:
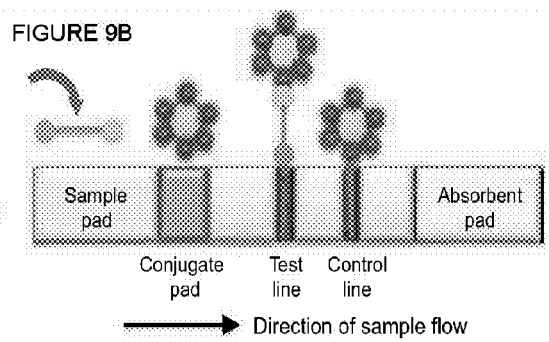
Figure 9C:
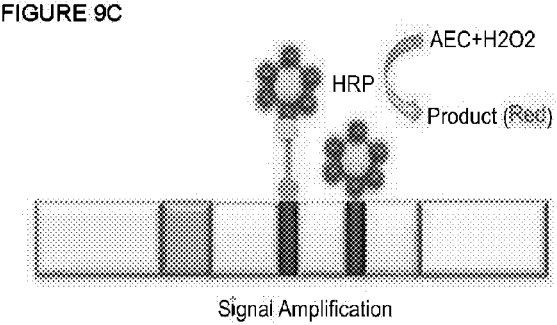
Figure 9D:
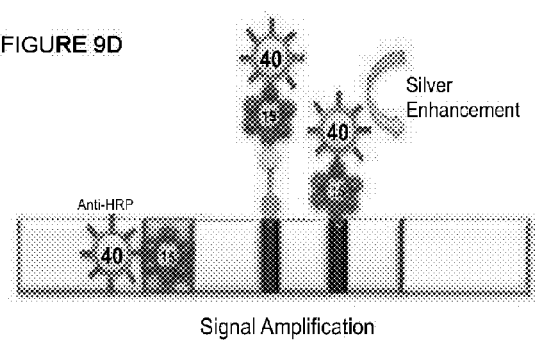

In some other embodiments, e.g. those illustrated in FIGS. 7, 8 and 9, signal amplification is enhanced by the use of horse radish peroxidase (HRP). The transfer reaction transfers a reporter group (e.g. biotin, antigen, or antibody) from a target-hybridized A probe to a target-hybridized G probe modified with a FITC at the 3'-end (FIG. 8). The reaction mix is added to the sample pad. The reaction mix flows into the conjugation pad where anti-FITC-GNP-HRP is conjugated to a FITC moiety (yellow circle) at the 3'-end of the G probe. Next, the G-probes labeled with the reporter group are retained on the test line by a complementary binding group (e.g. streptavidin, antigen, or antibody on the test line). GNP-EIRP without oligonucleotides are retained at the control line by an antibody to goat proteins. GNP and HRP provide signal amplification. In another embodiment, the GNP signal is enhanced by the use of silver staining (FIG. 9D)

4. Automated 2DPN (Two-dimensional Paper Networks) TARA Card

A two-dimensional paper network (2DPN) may refer to a paper-based platform that utilizes the shape and spatial arrangement of the paper substrate to control a fluid flow and achieve an automated, multi-step processing. Such devices are made from, e.g. porous nitrocellulose, in which flow paths are physically cut from the parent sheet, typically using a $CO_2$ laser cutter. This method represents a simple way to create flow paths within the porous substrate and eliminates the need for patterning of additional materials to create hydrophobic barriers.

Enzyme based signal amplification, for example, using the horseradish peroxidase (HRP) system commonly implemented in ELISA could greatly improve limits of detection (LOD) if it could be made compatible for use in POC devices. The two main challenges to this are (1) the long-term stability of the HRP conjugated antibody and its substrate, and (2) the capability of the POC device to perform the sequential multistep processes needed for the enzyme-based signal amplification without added user steps.

In some embodiments, methods are provided allowing long-term elevated temperature dry storage of reagents for enzyme-based signal amplification, which utilize, for example, antibodies conjugated to horseradish peroxidase (HRP) and HRP substrate diaminobenzidine (DAB). Further, in this method, the dry reagents can be incorporated into a 2DPN device and utilized to perform an automated TARA-ELISA for detection of two different probes (e.g. biotin and FITC) in a sandwich immunoassay so as to target nucleic acid sequences. The dry preservation of enzyme-based signal amplification reagents is very valuable in a number of applications that use enzyme-based systems ranging from a laboratory to numerous POC settings.

In certain embodiments, a lateral flow strip for TARA is adapted for performing on-card ELISA (2DPN TARA) using dry reagents. FIG. 10A shows a folding 2DPN device with integrated dry reagent pads that performs an automated ELISA for TARA with a single user activation step.

According to some embodiments, e.g. that illustrated in FIG. 10, the device is a nitrocellulose (Millipore, Billerica, Mass.) assay membrane cut into a three-inlet network using a CO2 laser cutting system. The NeutrAvidin at a concentration of 1 mg/ml is patterned at the detection region of the membrane. The assay membrane along with a cellulose wicking pad (Millipore, Bellerica, Mass.) is housed on one side of a folding Mylar (Fraylock, San Carlos, Calif.) laminate material. The glass fiber pads with dry HRP-antibody, DAB substrate, and buffer pad are placed on the opposite side of the laminate housing such that when the device is closed, each pad will make contact with the appropriate inlet of the assay membrane.

In some embodiments, the molecular amplified sample is added to a pad containing dry HRP-antibody, PBST buffer containing sodium percarbonate is added to a pad containing dry DAB substrate, and PBST buffer is added to a buffer pad as a wash fluid. While on-device storage of sodium percarbonate is not done in this particular embodiment, it is sold in a dry form that is stable at room temperature. The sodium percarbonate can be stored as a powder in the 2DPN device at a convenient location, and would generate H2O2 upon dissolution.

After a certain time, e.g. two minutes to allow for reagent rehydration, the card is folded to initiate the sequential delivery of reagents through the detection zone. The G probe (FITC) complex with the HRP-antibody label moves through the first inlet and across the detection zone, followed by the DAB substrate plus hydrogen peroxide from the second inlet, and finally a wash buffer from the third inlet. FIG. 10B shows an exemplary result from an automated ELISA card. The signal from the DAB precipitate can be easily visualized and observable by eye at the detection zone. This method of on-card enzyme signal amplification can also be quantified using a webcam or a flat-bed scanner.

5. A Microfluidic Tara Platform with Microbeads and Fluorescent Nanoparticles for Multiplex In another aspect, affordable and portable multiplex platform (FIGS. 11. 12) can rapidly detect and analyze multiple RNA or other nucleic acid targets using a small disposable microfluidic device on which microfluidics, photonics, and electronics are integrated with other biochemistry techniques.

As shown in an illustrative and non-limiting embodiment shown in FIG. 11C, the reporter group (By shown as blue circle) is transferred from the M probe to the By probe by means of a thiol exchange reaction depicted in FIG. 11C. This reaction is dependent on the hybridization of the probes to adjacent sequences in the target nucleic acid such as DNA or RNA. The reaction combined a high catalytic activity of the target nucleic acid such as DNA or RNA with useful yields and no background in 30 minute timeframe of the assay.

In certain embodiments, a high-throughput multiplex diagnosis technique using various beads/particles sizes and/or multiple fluorescent colors is provided. As shown in an illustrative and non-limiting embodiment of FIG. 12, the diagnosis can signify each specific analyte (e.g. different flu viral RNAs) in combination with TARA reactions. This diagnosis technique can be implemented in a design on a microfluidic platform incorporating two approaches: (a) TARA with microbeads and fluorescent nanoparticles such as Brilliant Violets and (b) Combination of lab on a chip 'impedance measurement' to detect at least two different sizes of microbeads with Color-Space-Time (COST) coding technology to discriminate more than at least four fluorescent colors using a single photodetector. Therefore, for example, when the two probe system is used, it can can be multiplexed using various sizes and/or morphologies of beads with different reporter (such as different fluorescent moieties). This technique allows creation of, for example, eight or more different 'size-color' barcodes (i.e. a unique signature of read-out resulted from the combinatorial consideration of bead sizes and fluoresce thereof), each of which is indicative of different target nucleic acid sequences, resulting in an economically and technologically viable high-throughput multi-target RNA screening system for, e.g. flu diagnosis and begin applicable to any infectious disease.

The overall work principles and design of the device according to some embodiments of the invention are shown in FIGS. 11 and 12. Sequence-specific PNA oligonucleotides are conjugated to microbeads and fluorescent nanoparticles. See FIG. 11C. Different target RNAs are detected with sequence-specific PNA oligonucleotide-labeled beads of different sizes, and fluorescently labeled, sequence specific oligonucleotides that are subsequently bonded to the one group of the beads only when target RNA exists. There may be different groups of the beads and the beads in the same group may have a substantially similar size (or an average diameter) whereas the beads in different groups may have substantially different sizes to those in the other groups.

In some embodiments, a method utilizes a plurality of groups of beads. The beads in the same group may have a substantially same size whereas the beads in a different group may have a different size such that individual groups of the beads can be discernable based on their sizes. In addition, the fluorescence associated with each group of the beads can be identical or different. The combination of the size of the beads and the fluorescence associated with the individual groups of the beads can provide a unique signature, so-called a "barcode", each of which is assigned to a different target nucleic acid sequence. In other words, the presence of each target RNA can be represented by the specific bead size and fluorescent color corresponding to the target RNA. Its abundance can be represented by the number and fluorescent intensity of the beads represented by barcoded for a specific target RNA. Flowing these beads through an impedance and fluorescence detection system in FIG. 12E, each bead is read out by the impedance signal (FIG. 12B) and the fluorescent color is detected via a color-space-time (COST) coding technique, by the fluorescent signal (FIG. 12B). The ratios of the R (red), Y (yellow) and G (green) components of the fluorescent intensity uniquely determine the color. In combination with the bead size information, one can detect and quantify over eight target RNAs simultaneously using a simple disposable chip and instrument containing only one laser diode (λ=405 nm) or even by a low cost LED and a single photo-detector.

6. A Kit Utilizing TARA Reaction Platform

According to some embodiments, kits for determining the presence and/or level of an analyte comprising a target nucleic acid sequence are provided. The kit may comprise (a) a plurality of a first probe, the first probe comprising a first reporter which is capable of being transferred to a second probe, and a first nucleic acid region, said first nucleic acid region being complementary to a first part of the target nucleic acid sequence, and (b) a plurality of a second probe, the second probe comprising a second nucleic acid region complementary to a second, different part of the target nucleic acid sequence, said first part and said second part of the target nucleic acid sequence being substantially adjacent to each other in the target nucleic acid sequence. The plurality of the second probe may be associated with one or more nano- or micro-particles. In the presence of the target nucleic acid sequence, the first reporter group in the first probe may be transferred to the second probe. In the presence of the target nucleic acid sequence, the first reporter group in the first probe is transferred to the second probe, resulting in a plurality of the first reporter group being transferred to the second probe. In addition, in some embodiments, the plurality of the first reporter group transferred to the second probe provides sufficient sensitivity such that no nucleic acid extraction and amplification is performed with the analyte is necessary.

In certain embodiments, the second probe in the kit comprises one or more selected from the group consisting of a gold nanoparticle, a silver nanoparticle, a microbead, and any mixtures thereof.

In some embodiments the first probe in the kit comprises the structure (VIII)

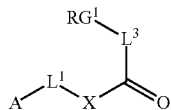

X is S, O, Se, S—C(O), O—C(O), Se—C(O), or $P^+R^1R^2$, wherein the C(O) group, if present, is bound to $L^1$;

$R^1$ and $R^2$, if present, are independently selected from the group consisting of aryl and alkyl;

$L^1$ is a linker or a bond; $L^3$ is a linker or a bond;

A comprises a nucleic acid region, which is complementary to a first nucleic acid region of the target nucleic acid sequence, and optionally a second reporter group which is linked to said region via a covalent bond or a linker.

In some embodiments the second probe in the kit comprises the structure (IX) or (X)

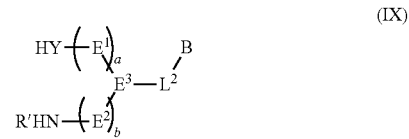

wherein $E^1$ and $E^2$ are independent of each other CHR", R" being a hydrogen, alkyl, alkenyl, alkynyl, cycloalkyl, heterocycloalkyl, aryl, heteroaryl, aralkyl, or a heteroaralkyl group;

$E^3$ is selected from the group consisting of alkyl, alkenyl, heteroalkyl, and heteroalkenyl, cycloalkyl, heterocycloalkyl, alicyclic system, aryl or heteroaryl group; optionally substituted; and wherein $E^1$ and $E^2$ are attached to the same or to adjacent carbon and/or nitrogen atom(s);

R' is hydrogen, an alkyl, alkenyl, alkynyl, cycloalkyl, heterocycloalkyl, aryl, heteroaryl, aralkyl, or a heteroaralkyl group;

Y is S, or Se;

$L^2$ is a linker or a bond;

B comprises a nucleic acid region, which is complementary to a second nucleic acid region of the target nucleic acid sequence, and optionally a first reporter group which is linked to said region via a covalent bond or a linker;

and one of a and b is 1 and the other one is 0 or both a and b are 1 or one of a and b is 2 and the other one is O;

or (X)

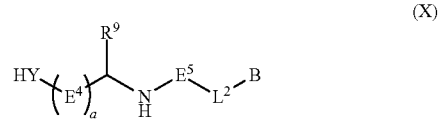

wherein $E^4$ in each instance is independently CHR", wherein R" is hydrogen, an alkyl, alkenyl, alkynyl, cycloalkyl, heterocycloalkyl, aryl, heteroaryl, aralkyl, or a heteroaralkyl group, optionally substituted;

$E^5$ is CHR'" or CR'", wherein R'" is hydrogen, an alkyl, alkenyl, alkynyl, cycloalkyl, heterocycloalkyl, aryl, heteroaryl, aralkyl, or a heteroaralkyl group, optionally substituted;

$R^9$ is hydrogen; alkyl; alkenyl; alkynyl; cycloalkyl; hetero-cycloalkyl; aryl; heteroaryl; aralkyl; or a heteroaralkyl group; optionally substituted or $R^9$ and R'" are taken together to form a heterocycloalkyl, alicylic system or heteroaryl, optionally substituted;

Y is S, or Se;

$L^2$ is a linker or a bond;

B comprises a nucleic acid region, which is complementary to a second nucleic acid region of the target nucleic acid sequence, and optionally a first reporter group which is linked to said region via a covalent bond or a linker; and a is 1 or 2.

According to some embodiments, methods for detecting a target nucleic acid directly from a sample, without nucleic acid extraction, comprising a plurality of nucleic acids of differing sequences, at least one target nucleic acid are provided. A method may comprise the steps of: contacting the sample nucleic acids with a plurality of probes, with at least one probe set for each nucleic acid target sequence comprising: a probe 1 comprising a first reporter group, which is capable of being transferred to a probe 2, and a region, which is complementary to a first region of the target nucleic acid sequence, and a probe 2 comprising a region, which is complementary to a second region of the target nucleic acid sequence and a moiety which is capable of receiving said first reporter group when both probe 1 and probe 2 hybridize to the target nucleic acid, wherein said second region of the target nucleic acid sequence is adjacent to the first region of the target nucleic acid; exposing the sample to conditions which lead to the transfer of the first reporter group of probe 1 to probe 2 in the presence of target nucleic acid; and detecting probe 2 molecules to which said first reporter group has been transferred.

In some embodiments, the region of the probe 1 complementary to a first region of the target nucleic acid is selected from the group consisting of DNA, RNA, PNA, PS-DNA, OMe-RNA, MOE-RNA, NP, PANA, LNA, MF, CeNA and tcDNA. Also, in some embodiments, probe 1 comprises a second reporter group. Also, in certain embodiments, the region of probe 2 complementary to a second region of the target nucleic acid is selected from the group consisting of DNA, RNA, PNA, PS-DNA, OMe-RNA, MOE-RNA, NP, PANA, LNA, MF, CeNA and tcDNA. In still another embodiment, probe 2 comprises a first reporter group.

In some embodiments, the probe set further comprises a probe 3, which comprises a nucleic acid region which is complementary to a third region of the target nucleic acid, probe 3 optionally comprising a first reporter group, wherein said third region is adjacent to the first region of the target nucleic acid or to the second region of the target nucleic acid.

In some other embodiments, the one or more reporter groups are selected from the group consisting of a fluorescent moiety, a quenching moiety, a donor fluorescent moiety, an acceptor fluorescent moiety capable to fluoresce upon transfer of energy from a donor fluorescent moiety, a radioactive moiety, a binding moiety, wherein the one or more reporter groups are chosen in such that the transfer of a first reporter group of probe 1 and/or the transfer of a second reporter group of the probe 1 allows detection of probe 2 and/or probe 3.

According to some embodiments, (a) the first reporter group of probe 1 comprises a fluorescent moiety and the second reporter group of probe 1 comprises a fluorescence quenching moiety; (b) the first reporter group of probe 1 comprises a donor fluorescent moiety and the second reporter group of probe 1 comprises an acceptor fluorescent moiety capable to fluoresce upon transfer of energy from the donor fluorescent moiety; (c) the first reporter group of probe 1 comprises an acceptor fluorescent moiety capable to fluoresce upon transfer of energy from a donor fluorescent moiety and the second reporter group of probe 1 comprises a donor fluorescent moiety; (d) the first reporter group of probe 1 comprises a fluorescent moiety and the first reporter group of probe 2 comprises a fluorescence quenching moiety; (e) the first reporter group of probe 1 comprises a fluorescence quenching moiety and the first reporter group of probe 2 comprises a fluorescent moiety; (f) the first reporter group of probe 1 comprises a donor fluorescent moiety and the first reporter group of probe 2 comprises an acceptor fluorescent moiety capable to fluoresce upon transfer of energy from the donor fluorescent moiety; (g) the first reporter group of probe 2 comprises a donor fluorescent moiety and the first reporter group of probe 1 comprises an acceptor fluorescent moiety capable to fluoresce upon transfer of energy from the donor fluorescent moiety; (h) the first reporter group of probe 1 comprises a fluorescence quenching moiety, the second reporter group of probe 1 comprises a fluorescent moiety, and the first reporter group of probe 2 comprises a fluorescent moiety, wherein both fluorescent moieties have different absorption and/or emission spectra; (i) the first reporter group of probe 1 comprises a donor fluorescent moiety, the second reporter group of probe 1 comprises an acceptor fluorescent moiety capable to fluoresce upon transfer of energy from the donor fluorescent moiety, and the first reporter group of probe 2 comprises a fluorescence quenching moiety; (j) the second reporter group of probe 1 comprises a donor fluorescent moiety, the first reporter group of probe 1 comprises an acceptor fluorescent moiety capable to fluoresce upon transfer of energy from the donor fluorescent moiety, and the first reporter group of probe 2 comprises a fluorescence quenching moiety; (k) the first reporter group of probe 1 comprises a donor fluorescent moiety, the first reporter group of probe 2 comprises an acceptor fluorescent moiety capable to fluoresce upon transfer of energy from the donor fluorescent moiety and the second reporter group of probe 1 comprises a fluorescence quenching moiety; (l) the first reporter group of probe 2 comprises a donor fluorescent moiety, the first reporter group of probe 1 comprises an acceptor fluorescent moiety capable to fluoresce upon transfer of energy from the donor fluorescent moiety, and the second reporter group of probe 1 comprises a fluorescence quenching moiety; (m) the second reporter group of probe 1 comprises a donor fluorescent moiety, the first reporter group of probe 1 comprises an acceptor fluorescent moiety capable to fluoresce upon transfer of energy from the donor fluorescent moiety, and the first reporter group of probe 2 comprises an acceptor fluorescent moiety capable to fluoresce upon transfer of energy from the acceptor fluorescent moiety of the first reporter group of probe 1; (n) the first reporter group of probe 1 comprises a donor fluorescent moiety, the second reporter group of probe 1 comprises an acceptor fluorescent moiety capable to fluoresce upon transfer of energy from the donor fluorescent moiety, and the first reporter group of probe 2 comprises an acceptor fluorescent moiety capable to fluoresce upon transfer of energy from the donor fluorescent moiety, wherein both acceptor fluorescent moieties have different absorption and/or emission spectra; (o) the first reporter group of probe 2 comprises a donor fluorescent moiety, the first reporter group of probe 1 comprises an acceptor fluorescent moiety capable to fluoresce upon transfer of energy from the donor fluorescent moiety, and the second reporter group of probe 1 comprises an acceptor fluorescent moiety capable to fluoresce upon transfer of energy from the acceptor fluorescent moiety of the first reporter group of probe 1; or (p) the second reporter group of probe 1 comprises a donor fluorescent moiety, the first reporter group of probe 2 comprises a donor fluorescent moiety, and the first reporter group of probe 1 comprises an acceptor fluorescent moiety capable to fluoresce upon transfer of energy from either of the two donor fluorescent moieties or from both of the two donor fluorescent moieties, wherein both donor fluorescent moieties have different absorption and/or emission spectra.

In certain embodiments, the fluorescent moiety is selected from the group consisting of fluorescein isothiocyanate (FITC), tetramethylrhodamine isothiocyanate (TRITC), phycoerythrin, Cy7, fluorescein (FAM), Cy3, Cy3. 5, Texas Red, LightCycler-Red 640, LightCycler Red 705, tetramethylrhodamine (TMR), rhodamine derivative (ROX), hexachlorofluorescein (HEX), Cy5, Cy5.5, rhodamine 6G (R6G), the rhodamine derivative JA133, Alexa Fluor 488, Alexa Fluor 546, Alexa Fluor 633, Alexa Fluor 555, Alexa Fluor 647, fluorescent nanoparticles, and fluorescent transition metal complexes.

In some embodiments, the fluorescence quenching moiety is 4-(4'-dimethyl-aminophenylazo)benzoic acid (dabcyl), black hole quencher 1 (BHQ-1), black hole quencher 2 (BHQ-2), QSY-7, or QSY-35, or it is selected from the group of FRET pair acceptors consisting of TRITC, Cy7, Cy3, Cy3.5, Texas Red, LightCycler-Red 640, Light-Cycler Red 705, TMR, ROX, HEX, Cy5, Cy5.5, the rhodamine derivative JA133, Alexa Fluor 546, Alexa Fluor 633, and Alexa Fluor 647.

In some other embodiments, the donor fluorescent moiety is selected from the group consisting of FITC, phycoerythrin, FAM, Cy3, Cy3.5, R6G, TMR, Alexa Fluor 488, and Alexa Fluor 555.

In some additional embodiments, the radioactive moiety is selected from the group consisting of 32P, 33P, 35S, 123I, 18F, 3H, 14C, and complexes of radioactive metals.

In still some additional embodiments, the binding moiety is selected from the group consisting of an antigenic peptide, an antigenic small molecule, antibody, biotin, and a His-tag.

In still some additional embodiments, a combination of the donor fluorescent moiety and the acceptor fluorescent moiety capable to fluoresce upon transfer of energy from the donor fluorescent moiety is selected from the group consisting of:

(a) FITC and TRITC;
(b) phycoerythrin and Cy7;
(c) FAM and TMR; and
(d) Alexa Fluor 488 and Alexa Fluor 546.

In still some additional embodiments, probe 2 molecules to which the first reporter group of probe 1 has been transferred are detected by the fluorescence signal of the first reporter group, by the quenching effect of the first reporter group, by the fluorescence signal of the first reporter group of probe 2, by binding of an optionally labelled antibody, by the radioactive signal, and/or by the binding of streptavidin.

According to some embodiments, a reporter group is transferred from the probe 1 to probe 2 and/or to probe 3 by a chemical reaction selected from the group consisting of:

(a) substitution at the carbonyl carbon atom as depicted in reaction scheme (I):

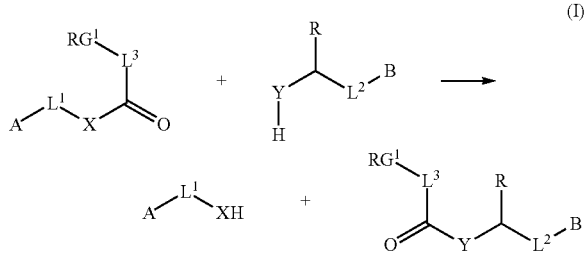

wherein
RC is a first reporter group;
X is S, O, Se, S—C(O), O—C(O), Se—C(O), or P$^+$R$^1$R$^2$, wherein the C(O) group, if present, is bound to L$^1$;
Y is NH, S, N—R$^4$, HN—O, NR$^4$—NR$^5$, O, O—O, O—NH, S—S, S—O, PR$^3$, P(OR$^3$), Se, or a C nucleophile, wherein the S—O group is oriented in such that the O is bound to the carbon atom carrying the R group;

R is hydrogen, an alkyl, alkenyl, alkynyl, cycloalkyl, heterocycloalkyl, aryl, heteroaryl, aralkyl, or a heteroaralkyl group, optionally substituted;

R$^1$, R$^2$, and R$^3$, if present, are independently selected from the group consisting of aryl and alkyl;

R$^4$ and R$^5$, if present, are independently from each other hydrogen, an alkyl, alkenyl-, alkynyl, cycloalkyl, heterocycloalkyl, aryl, heteroaryl, aralkyl, or a heteroaralkyl group, optionally substituted;

L$^1$ is a linker or a bond; L$^2$ is a linker or a bond; L$^3$ is a linker or a bond;

A comprises a nucleic acid region, which is complementary to a first nucleic acid region of the target nucleic acid sequence, and optionally at least a second reporter group which is linked to said region via a covalent bond or a linker; and B comprises a nucleic acid region, which is complementary to a second nucleic acid region of the target nucleic acid sequence, and optionally at least a first reporter group which is linked to said region via a covalent bond or a linker;

(b) substitution at the alkyl carbon atom as depicted in reaction scheme (II):

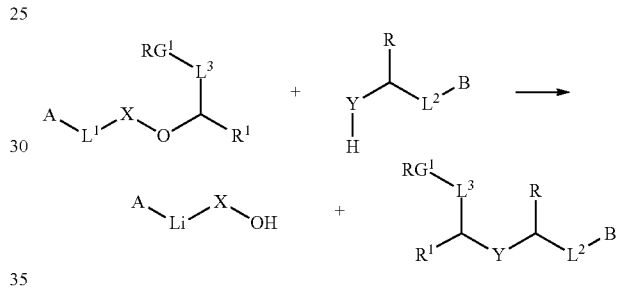

wherein RG$^1$ is a reporter group;
X is SO$^2$ or P$^+$R$^1$R$^2$;
Y is NH, S, S—PO, N—R$^5$, HN—O, NR$^5$—NR$^6$, O, O—O, ONH, S—S, S—O, PR$^4$, P(OR$^4$), Se, Se—PO$^3$, S—O are oriented in such that the —PO$^3$ moiety or the O atom is bonded to the carbon atom carrying the R residue and S and Se are bonded to H before the reaction and to the carbon atom linked to L$^3$ after the reaction;

R is hydrogen, an alkyl, alkenyl, alkynyl, cycloalkyl, heterocycloalkyl, aryl, heteroaryl, aralkyl, or a heteroaralkyl group, optionally substituted;

R$^1$ is —CN, —NO$_2$, —COOAlk, —H, —CHO, —COAlk;

R$^2$, R$^3$, and R$^4$, if present, are independently from each other aryl and alkyl;

R$^5$ and R$^6$, if present, are independently from each other hydrogen, an alkyl, alkenyl, alkynyl, cycloalkyl, heterocycloalkyl, aryl, heteroaryl, aralkyl, or a heteroaralkyl group, optionally substituted;

L$^1$ is a linker or a bond; L$^2$ is a linker or a bond; L$^3$ is a linker or a bond;

A comprises a nucleic acid region, which is complementary to a first nucleic acid region of the target nucleic acid sequence, and optionally a second reporter group which is linked to said region via a covalent bond or a linker; and B comprises a nucleic acid region, which is complementary to a second nucleic acid region of the target nucleic acid sequence, and optionally a first reporter group which is linked to said region via a covalent bond or a linker;

(c) substitution at phosphate as depicted in reaction scheme (III):

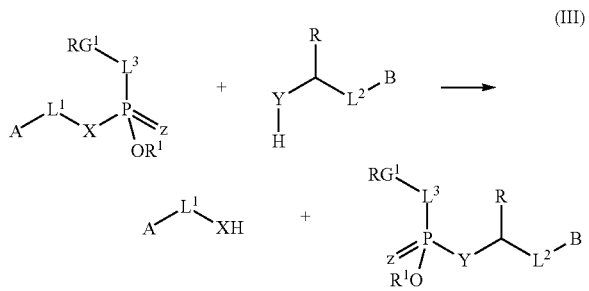

wherein RG$^1$ is a reporter group;
X is O, NR$^2$, or S;
Y is O, NH, Se or S;
Z is not present or O;
R and R$^1$ are independently from each other hydrogen, an alkyl, alkenyl, alkynyl, cycloalkyl, heterocycloalkyl, aryl, heteroaryl, aralkyl, or a heteroaralkyl group, optionally substituted;
R$^2$, if present, is hydrogen, an alkyl, alkenyl, alkynyl, cycloalkyl, heterocycloalkyl, aryl, heteroaryl, aralkyl, or a heteroaralkyl group, optionally substituted;
L$^1$ is a linker or a bond; L$^2$ is a linker or a bond; L$^3$ is a linker or a bond;
A comprises a nucleic acid region, which is complementary to a first nucleic acid region of the target nucleic acid sequence, and optionally a second reporter group which is linked to said region via a covalent bond or a linker; and
B comprises a nucleic acid region, which is complementary to a second nucleic acid region of the target nucleic acid sequence, and optionally a first reporter group which is linked to said region via a covalent bond or a linker;
(d) Staudinger reaction as depicted in reaction scheme (IV):

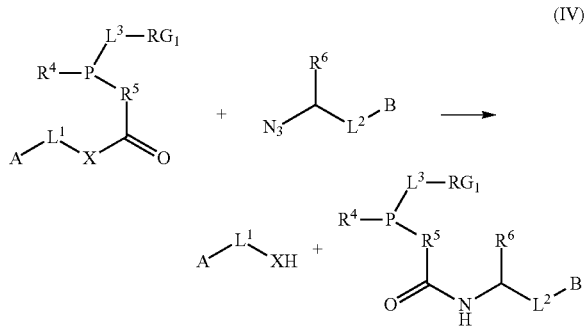

wherein RG$_1$ is a reporter group;
X is O, S, Se, or NR$^3$, wherein R$^3$ is H or alkyl;
R$^4$ is hydrogen, an alkyl, alkenyl, alkynyl, cycloalkyl, heterocycloalkyl, aryl, heteroaryl, aralkyl, or a heteroaralkyl group, optionally substituted;
R$^5$ is an alkyl, alkenyl, alkynyl, cycloalkyl, heterocycloalkyl, aryl, heteroaryl, aralkyl, or a heteroaralkyl group, optionally substituted;
R$^6$ is hydrogen, an alkyl, alkenyl, alkynyl, cycloalkyl, heterocycloalkyl, aryl, heteroaryl, aralkyl, or a heteroaralkyl group, optionally substituted;
L$^1$ is a linker or a bond; L$^2$ is a linker or a bond; L$^3$ is a linker or a bond;
A comprises a nucleic acid region, which is complementary to a first nucleic acid region of the target nucleic acid sequence, and optionally a second reporter group which is linked to said region via a covalent bond or a linker; and
B comprises a nucleic acid region, which is complementary to a second nucleic acid region of the target nucleic acid sequence, and optionally a first reporter group which is linked to said region via a covalent bond or a linker;
(e) Wittig reaction as depicted in reaction scheme (V):

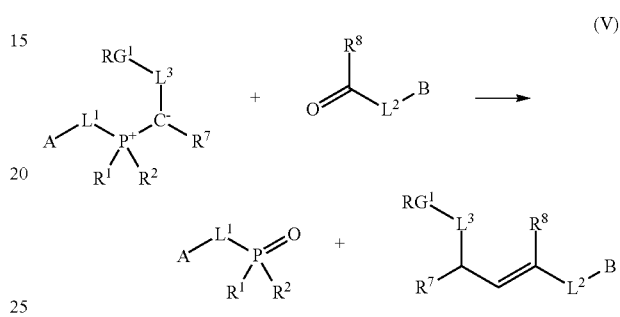

wherein RG$^1$ is a reporter group;
R$^1$ and R$^2$ are independently from each other selected from the group consisting of hydrogen, an alkyl, alkenyl, alkynyl, cycloalkyl, heterocycloalkyl, heteroaryl, aralkyl, and a heteroaralkyl group, optionally substituted;
R$^7$ is C(O)N-alkyl, NO$_2$, CN, C(O)-alkyl, C(O)O-alkyl, aryl, heteroaryl, fluorinated alkyl;
R$^5$ is hydrogen, CH=CH$_2$, aryl, alkyl;
L$^1$ is a linker or a bond; L$^2$ is a linker or a bond; L$^3$ is a linker or a bond;
A comprises a nucleic acid region, which is complementary to a first nucleic acid region of the target nucleic acid sequence, and optionally a second reporter group which is linked to said region via a covalent bond or a linker; and
B comprises a nucleic acid region, which is complementary to a second nucleic acid region of the target nucleic acid sequence, and optionally a first reporter group which is linked to said region via a covalent bond or a linker.
In certain embodiments, the one or more linkers from the above compounds are selected from the group consisting of an alkyl, alkenyl, alkynyl, cycloalkyl, heterocycloalkyl, aryl, heteroaryl, aralkyl, and a heteroaralkyl group, optionally substituted.
In some embodiments, the second probe is represented by formula (VI)

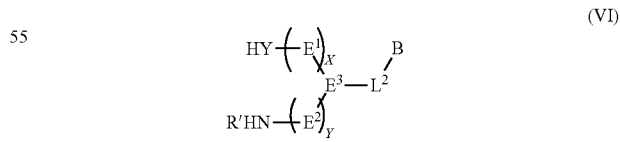

wherein
E$^1$ and E$^2$ are independent of each other CHR″, wherein R″ is hydrogen, alkyl, alkenyl, alkynyl, cycloalkyl, heterocycloalkyl, aryl, heteroaryl, aralkyl, or a heteroaralkyl group;
E$^3$ is selected from the group consisting of alkyl, alkenyl, heteroalkyl, and heteroalkenyl, cycloalkyl, heterocycloalkyl, alicyclic system, aryl or heteroaryl group; optionally substituted; and wherein E' and $E^2$ are attached to the same or to adjacent carbon and/or nitrogen atom(s);

R' is hydrogen, an alkyl, alkenyl, alkynyl, cycloalkyl, heterocycloalkyl, aryl, heteroaryl, aralkyl, or a heteroaralkyl group;

$L^2$ is a linker or a bond;

B comprises a nucleic acid region, which is complementary to a second nucleic acid region of the target nucleic acid sequence, and optionally a first reporter group which is linked to said region via a covalent bond or a linker;

Y is S or Se; and one of X and Y is 1 and the other one is 0 or both X and Y are 1 or one of X and Y is 2 and the other one is O;

or formula (VII):

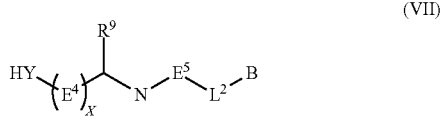

(VII)

wherein $E^4$ in each instance is independently CHR", wherein R" is hydrogen, an alkyl, alkenyl, alkynyl, cycloalkyl, heterocycloalkyl, aryl, heteroaryl, aralkyl, or a heteroaralkyl group, optionally substituted;

$E^5$ is CHR''' or CR''', wherein R''' is hydrogen, an alkyl, alkenyl, alkynyl, cycloalkyl, heterocycloalkyl, aryl, heteroaryl, aralkyl, or a heteroaralkyl group, optionally substituted;

$R^9$ is hydrogen; alkyl; alkenyl; alkynyl; cycloalkyl; heterocycloalkyl; aryl; heteroaryl; aralkyl; or a heteroaralkyl group; optionally substituted or R9 and R''' are taken together to form a heterocycloalkyl, alicylic system or heteroaryl; optionally substituted;

$L^2$ is a linker or a bond;

B comprises a nucleic acid region, which is complementary to a second nucleic acid region of the target nucleic acid sequence, and optionally a first reporter group which is linked to said region via a covalent bond or a linker; and Y is S or Se; and x is 1 or 2.

In some embodiments, the distance between the first region and the second region of the target nucleic acid and/or the distance between the first and the third region and/or the distance between the second and the third region ranges from 0 to 10 nucleotides.

In some embodiments, the method may comprise an additional step of detecting probe 1 and/or probe 3.

In some embodiments, the method may comprise one or more of the following additional steps:

(iv) contacting a probe 1 and a probe 2 in a separate sample, which does not contain the target nucleic acid sequence, and (v) detecting probe 1 molecules from which said first reporter group has been transferred and/or probe 2 molecules to which said first reporter group has been transferred.

In some embodiments, probe 2 is temporarily or permanently immobilized, retained, or held on a stationary phase.

In some embodiments, the method may further comprise a washing step carried out after step (ii) which removes the sample and probe 1.

In some embodiments, a third probe is added to the sample prior, during or after the transfer of the reporter group from probe 1 to probe 2.

In some embodiments, the target nucleic acid is DNA or RNA.

In some embodiments, the target nucleic acid is a prokaryotic, viral or eukaryotic nucleic acid.

In some embodiments, the target nucleic acid contains a single nucleotide polymorphism (SNP).

In some embodiments, the target nucleic acid is a splice variant of a naturally occurring nucleic acid.

In some embodiments, the method is for determining the sequence of a target nucleic acid.

In some embodiments, the method is for the detection of at least one single nucleotide polymorphism in at least one target nucleic acid.

In some embodiments, the method is for the detection of at least one target nucleic acid from at least one pathogenic organism, preferably a virus, a bacterium, a fungus.

In some embodiments, the method is for the detection of at least one target nucleic acid from at least one organism causing allergic reactions.

In some embodiments, probe 2 molecule to which said first reporter group has been transferred contains a gold nanoparticle.

In some embodiments, the detectable nanoparticle is chemically detectable, optically detectable, or electrochemically detectable.

In some embodiments, the gold nanoparticle is immobilized to a stationary phase by the reporter group in probe 2 to which an antigenic moiety is transferred.

In some embodiments, the detectable nanoparticle comprises SERS-active nanoparticles, fluorescent nanoparticles, quantum dots, or combinations thereof.

In some embodiments, the SERS-active nanoparticle comprises a gold nanoparticle, silver nanoparticle, or combinations thereof.

In some embodiments, the stationery phase is a lateral flow paper strip.

In some embodiments, the stationery phase is a 2DPN (Two-dimensional paper networks) device.

In some embodiments, the stationery phase is a microfluidic device.

In some embodiments, the stationery phase is a microbeads.

In some embodiments, the stationery phase is a fluorescent nanoparticles.

In some embodiments, the microbeads to a stationary phase by the reporter group in probe 2 to which a fluorescent moiety is transferred.

According to some embodiments, a kit for detecting at least one target nucleic acid sequence in a sample comprising one probe set for each target nucleic acid sequence is provided. The probe set may comprise:

(a) a probe 1 having the structure (VI)

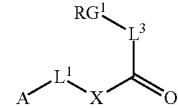

X is S, O, Se, S—C(O), O—C(O), Se—C(O), or $P^+R^1R^2$, wherein the C(O) group, if present, is bound to $L^1$;

$R^1$ and $R^2$, if present, are independently selected from the group consisting of aryl and alkyl;

$L^1$ is a linker or a bond; $L^3$ is a linker or a bond;

A comprises a nucleic acid region, which is complementary to a first region of the target nucleic acid sequence, and optionally a second reporter group which is linked to said region via a covalent bond or a linker; and (b) a probe 2 having the structure (VII) or (VIII)

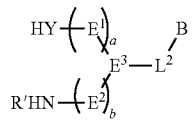

wherein

E1 and E2 are independent of each other CHR", R" being a hydrogen, alkyl, alkenyl, alkynyl, cycloalkyl, heterocycloalkyl, aryl, heteroaryl, aralkyl, or a heteroaralkyl group;

E3 is selected from the group consisting of alkyl, alkenyl, heteroalkyl, and heteroalkenyl, cycloalkyl, heterocycloalkyl, alicyclic system, aryl or heteroaryl group; optionally substituted; and wherein E1 and E2 are attached to the same or to adjacent carbon and/or nitrogen atom(s);

R' is hydrogen, an alkyl, alkenyl, alkynyl, cycloalkyl, heterocycloalkyl, aryl, heteroaryl, aralkyl, or a heteroaralkyl group;

Y is S, or Se;

L2 is a linker or a bond;

B comprises a nucleic acid region, which is complementary to a second region of the target nucleic acid sequence, and optionally a first reporter group which is linked to said region via a covalent bond or a linker; and one of a and b is 1 and the other one is 0 or both a and b are 1 or one of a and b is 2 and the other one is 0;

or

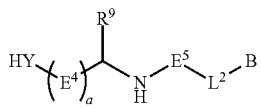
VIII wherein

E4 in each instance is independently CHR", wherein R" is hydrogen, an alkyl, alkenyl, alkynyl, cycloalkyl, heterocycloalkyl, aryl, heteroaryl, aralkyl, or a heteroaralkyl group, optionally substituted;

E5 is CUR'" or CR'", wherein R'" is hydrogen, an alkyl, alkenyl, alkynyl, cycloalkyl, heterocycloalkyl, aryl, het R9 is hydrogen; alkyl; alkenyl; alkynyl; cycloalkyl; heterocycloalkyl; aryl; heteroaryl; aralkyl; or a heteroaralkyl group; optionally substituted or R9 and R'" are taken together to form a heterocycloalkyl, alicylic system or heteroaryl; optionally substituted;

Y is S, or Se;

L2 is a linker or a bond;

B comprises a nucleic acid region, which is complementary to a second region of the target nucleic acid sequence, and optionally a first reporter group which is linked to said region via a covalent bond or a linker; and a is 1 or 2;

wherein the second region of the target nucleic acid sequence is adjacent to the first region of the target nucleic acid.

In some embodiments, in the kit, the regions which are complementary to the first region of the target nucleic acid sequence or to the second region of the target nucleic acid sequence are independently selected from the group consisting of DNA, RNA, PNA, PS-DNA, OMe-RNA, MOE-RNA, NP, PANA, LNA, MF, CeNA and tcDNA.

In some embodiments, in the kit, probe 1 comprises a second reporter group.

EXAMPLES

Example 1

Rapid Point-of-Care Diagnostic for Early Detection of Dengue Infection

There are 230 million cases of dengue virus infection a year, including 21,000 deaths worldwide. Dengue fever is one of the most important mosquito-borne diseases affecting people in more than 110 countries globally mostly in tropical and sub-tropical regions of Asia, Africa, and Central and South America. Dengue viruses are classified into four serotypes (DENY-1, DENV-2, DENV-3, and DENV-4). Immunity to one type that circulates, DENV-1 through -4, does not prevent illness from another type and can exacerbate subsequent disease with another type. Dengue fever can be a mild infection, but other dengue hemorrhagic fever (DHF) and dengue shock syndrome (DSS) can cause death at a high rate.

There are unmet needs for an earlier detection of dengue at the point-of-care (POC). Unfortunately, current diagnostics for dengue use at the point-of-care (POC) settings are mainly ELISA based immunological assays that often lack sufficient sensitivity, specificity, and multiplex capacity for accurate early diagnosis. The main disadvantage of ELISA based POC test is that the antibodies used in these tests are generated several days after the first clinical symptoms appear. To address this problem, several RT-PCR assays have previously been developed for early dengue detection and serotype identification with a high level of sensitivity and specificity. Moreover, the product was already well developed by the Center for Disease Control (CDC) as FDA approved CDC DENV-1-4 Real-Time RT-PCR assay for detection and serotype identification of dengue virus. Performance characteristics have been well determined by CDC.

Reverse transcription-loop-mediated isothermal amplification (RT-LAMP) is a recently developed technique for POC setting with similar detection sensitivity and specificity comparable to RT-PCR based assays, but only needs a single temperature, not requiring PCR thermo-cycler machine. Furthermore, the enzymes that are routinely used for target amplification in molecular diagnostic testing are unable to amplify RNA directly, and the Reverse Transcriptase enzyme that is used to convert RNA to cDNA usually requires the input of purified RNA. The processing steps associated with isolating and purifying RNA are very costly and time consuming. If the dengue diagnostic kit can detect the presence of the virus directly from a patient sample on the first day, without laboratory processing, thereby saving valuable time of the patient, this kit would present a bigger advantage in saving lives and reducing suffering over currently available technologies.

The early stage, dengue fever symptoms can resemble infection from another disease (such as malaria, chikungunya, leptospirosis, typhoid, typhus and rickettsial diseases) such that the effective dengue diagnostic should be able to distinguish dengue from other diseases having similar clinical presentations. Therefore, there is an urgent requirement for early detection and specific, sensitive and inexpensive dengue diagnostic tools at the point-of-care settings that can be used in the field. The development of new techniques for the early detection and simplified detection POC tests are very important for accurate diagnosis of dengue for proper care and treatment for the patients.

As discussed above, a diagnostic tool is described here that is based upon a novel chemistry platform technology using Template Assisted Rapid Assay (TARA), an enzyme-free, PCR-less and rapid transfer reaction assay directly from whole blood or other samples. The illustrative Example 1 provided herewith is based on the DENV-1-4 Real-Time RT-PCR primer sequences and utilized the CLT-direct PNA probe sets that are designed to target four distinct serotypes (DENY-1, DENV-2, DENV-3, and DENV-4) of dengue virus.

Therefore, a rapid dengue detection kit based on an innovative TARA technology is developed and it is instrumentation-free, low cost, disposable, rapid and sensitive nucleic acid POC diagnostic device capable of detecting and identifying the four different serotypes of dengue virus. This approach has good potential as a platform technology for a rapid, sensitive and low-cost POC diagnosis of many other infectious diseases. An innovative, rapid, and "PCR-free" detection technology in TARA may improve the early detection of dengue outbreaks.

Template Assisted Rapid Assay (TARA); Rapid dengue diagnosis assay development using an innovative RNA chemistry: A platform technology "TARA" using an innovative RNA chemistry for rapid, sensitive, enzyme-free, PCR-less and low-cost POC diagnosis of infectious diseases. The designed direct PNA probe sets target four distinct serotypes (DENY-1, DENV-2, DENV-3, and DENV-4) of dengue virus. PNAs can be easily synthesized and functionalized, and more stable and more responsive to point-mutations than their DNA counterpart. Several PNA probe combinations were evaluated experimentally to determine the optimized combination. For each target viral RNA, 2 PNA probe pairs [G-probe (magnetic gold nanoparticles) and A-probe (antibody)] were designed and evaluated. Probe design was performed via Primer Express version two software (Applied Biosystems). The software created the designed probe sets. Probe hybridization sequences were evaluated by BLAST to select regions conserved across multiple transcript variants. For initial design, target complexity and accessibility was evaluated using Visual OMP (DNA Software Inc.).

The data are shown in FIG. 13. TARA was sufficiently sensitive to detect 0.005 fmoles of a synthetic dengue RNA template by eye and/or a smartphone scanner using transfer reaction molecular amplification and GNP signal amplification alone on a lateral flow strip (See FIG. 13). Moreover, no background signal was detectable from no template control (non-templated transfer, FIG. 13A) or a single base mismatch RNA template (FIG. 13D). TARA detected dengue virus from plasma patient sample (FIG. 13C). The data shows that TARA can work directly on whole blood (FIG. 13E), saliva, urine or nasopharyngeal swab samples (FIG. 13F). The reaction conditions were 150 nM A probe, 100 nM G probe conjugated with GNP incubated at room temperature for 30 minutes in the CLBuffer.

According to some embodiments, an RNA stabilizing buffer can be used to keep the RNA stable for room temperature storage and transport over at least one week. One of the biggest challenges in point-of-care testing is the need for extensive sample preparation to extract the analyte of interest (e.g. RNA, DNA). The foregoing challenges can be overcome by using the non-enzymatic nucleic acid amplification technology called TARA which works in samples collected and stabilized.

Figure 15:
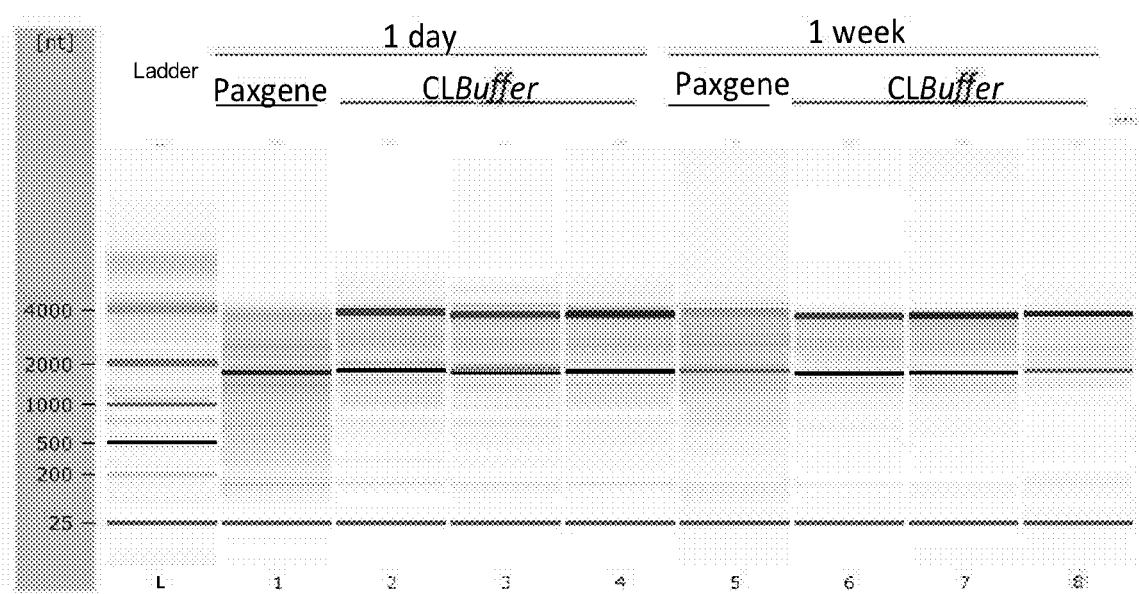
FIG. 15 shows gel images of RNA extracted with CLBuffer RNA from blood which was then stabilized in Paxgene or CLBuffer after one day or one week storage at room temperature. The figure is a Bioanalyzer gel trace showing the 28S RNA and the 18S RNA bands. The RNA extracted from CLBuffer was stable in 3 different samples as shown by the higher intensity of the longer 28 S RNA.

The stabilized RNA (FIG. 15), lysed cells or pathogens, and denatured the secondary structure in the RNA. Detection was linear with a correlation coefficient r2 of 0.93 at this low detection range (FIG. 13B). The reaction on RNA sample spiked into blood was not inhibited by blood (FIG. 13D). The test line bands were quantified by scanning in grayscale with VueScan App (Harrick Software) on iPhone 6 to a jpeg file which was opened and quantified in Adobe Photoshop v.CS5.1. The limit of detection of 0.005 fmoles corresponds to 107 copies of RNA/mL.

In certain assays, it may need a 103-fold enhancement to detect the clinically relevant 105 copies/mL of RNA from the virus. Moreover, a 100-fold enhancement is needed to detect 100,000 copies of RNA from the 100 pathogens (assuming 1000 copies of 18S rRNA in each pathogen). The horse radish peroxidase (HRP) was added to the GNP to achieve a 104 enhancement in signal which enabled the detection of 1000 copies of viral RNA (FIG. 14) and the detection of the 100,000 copies of RNA in 100 pathogens. Routinely, TARA using GNP-HRP double label yields 104 enhancement in signal (FIG. 14).

Alternatively, a dual gold nanoparticle conjugate-based lateral flow assay (102-fold) and silver enhancement (103-fold) can be used for improving the sensitivity up to 105-fold enhancement. In a dual GNP assay, after the 1st GNPs conjugate is captured on the LFB, the 2nd GNP conjugate binds on the 1st GNPs to amplify the optical signal by depositing more GNPs on the test zone which offering a 100-fold signal amplification.

Example 2

Point-of-Care Rapid RNA Diagnosis of Influenza Virus

Influenza rapidly spreads around the world in seasonal epidemics, where it will affect 5-15% of the population, and imposes a considerable economic hardship. Early detection, characterization, and risk assessment of Influenza viruses are critical to protecting public health. Global burdens from existing or emerging Influenza highlight the need for point-of-care (POC) diagnostics to enhance timely identification and intervention. To better prepare for the next pandemic, a simple and easy-to-use test is needed for characterizing newly emerging influenza viruses and fulfilling the needs of point-of-care flu diagnostic devices at low cost with multiplex capabilities.

Moreover, current point-of-care (POC) diagnostics for Influenza virus are ELISA (immunological assays) that often lacks adequate sensitivity, specificity, and multiplex capacity for an accurate, early diagnosis. The sensitivity of rapid ELISA POC kits range from 20-90% for seasonal influenza and 10-70% for the pandemic influenza strain A/H1N1 of 2009. To address this problem, several RT-PCR assays have been developed for influenza detection with a high level of sensitivity and specificity. According to the guideline for diagnosis of pandemic H1N1 by the Centers for Disease Control and Prevention (CDC, USA), the probable clinical case must be confirmed by either positive RT-PCR, or virus culture (CDC). Real-time RT-PCR is the recommended test for the diagnosis of pandemic H1N1. Performance characteristics have been well determined by CDC. These multiple independent steps and tests increase the processing time and cost for detection and identification. Furthermore, Real-time PCR requires expensive instrumentation, technical training and may take a 24 hour turnaround time. However, the enzymes that are routinely used for target amplification in molecular diagnostic testing are unable to directly amplify RNA. The reverse transcriptase enzyme that is used to convert RNA to cDNA usually requires the input of purified RNA. The processing steps associated with isolating and purifying RNA are very costly and time consuming. Reverse transcription-loop-mediated isothermal amplification (RT-LAMP) is a recently developed technique for POC setting but needs to convert RNA to cDNA using enzyme which requires refrigeration, the input of purified RNA, and expensive instruments.

Therefore, there is an urgent need for early detection, specific, sensitive and inexpensive Flu diagnostic tools at the point-of-care settings that can be used in the field. The development of new techniques for the early detection and simplified detection POC tests are very important for accurate diagnosis of Flu for proper care and treatment for the patients. The Template Assisted Rapid Assay (TARA) described herein can be used to diagnose flu. The TARA system is an enzyme-free, PCR-less and rapid transfer reaction assay directly from samples from nasopharyngeal swab, nasal aspirate, oropharyngeal swab or blood. Base on the CDC influenza A H1N1 (2009) Real-Time RT-PCR primer sequences, the designed, direct PNA probe sets targeting multiple RNA pathogens with typing and subtyping targeting the H1, H3, N1, N2 and matrix genes of influenza A virus and NS gene of influenza B virus were diagnosed.

A nucleic acid dipstick-based or microfluidic-based influenza A H1N1 POC diagnostic assay uses the RNA chemistry described herein. The product is based upon a platform technology using this novel chemistry, Template Assisted Rapid Assay (TARA) which provides a sensitive, enzyme-free, PCR-less, rapid, nucleic acid based POC diagnostic device capable of detection and identification of seasonal influenza and pandemic influenza. Currently, the most common form of POC testing is ELISA test. The market is already highly competitive as can see from the following: ELISA test kits (FDA cleared test)-SAS FluAlert Influenza A&B (SA Scientific), SAS FluAlert Influenza A; FluAlert Influenza B (SA Scientific), 3M Rapid Detection Flu A+B Test (Response Biomedical Corp. for 3M Healthcare), BinaxNOW Influenza A&B** (Inverness Medical), Remel X/pect Flu A&B (Thermo Fisher Scientific), TRUFLU (Meridian Bioscience Inc.), OSOM Influenza A&B (Sekisui Diagnostics), QuickVue Influenza A+B (Quidel Corp), BD Directigen EZ Flu A+B (Becton, Dickinson and Co.), and Status Flu A=B (Princeton BioMeditech Corp.). Especially, rapid POC antibody-based tests can miss 50 to 60% of cases of influenza. However, nucleic acid tests allow higher specificity and sensitivity compared to alternatives based on antibodies. TARA utilizes a chemical transfer reaction with similar detection sensitivity and specificity compared to RT-PCR assays, but allows a single temperature incubation and simple readout on paper-strip more suitable for field devices without enzyme, PCR, and instrument. TARA also offers the potential for detection in less pure samples, such as saliva or blood, facilitating a quick field sample preparation.

Other aspects will be clear to the skilled artisan, and need not be reiterated here. The terms and expression which have been employed are used as terms of description and not of limitation, and there is no intention in the use of such terms and expression of excluding any equivalents of the features shown and described or portions thereof, it being recognized that various modifications are possible within the scope of the invention.

What is claimed is:

1. A method of determining the presence and/or level of an analyte comprising a target nucleic acid sequence in a sample, the method comprising:
   contacting the sample with a mixture comprising at least one set of probes to provide a reaction mixture, the at least one set of probes comprising:
   a) a plurality of a first probe, the first probe comprising a first reporter group which is capable of being transferred to a second probe, and a first nucleic acid region, said first nucleic acid region being complementary to a first part of the target nucleic acid sequence,
   wherein the first probe comprises a structure

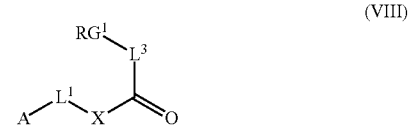

(VIII)

wherein $RG^1$ is the first reporter group;
   X is S, O, Se, S—C(O), O—C(O), Se—C(O), or $P^+R^1R^2$, wherein the C(O) group, if present, is bound to $L^1$; $R^1$ and $R^2$, if present, are independently selected from the group consisting of aryl and alkyl;
   $L^1$ is a linker or a bond;
   $L^3$ is a linker or a bond; and
   A comprises the first nucleic acid region, and
   b) a plurality of a second probe, the second probe comprising a second nucleic acid region complementary to a second, different part of the target nucleic acid sequence,
   wherein the second probe comprises a structure

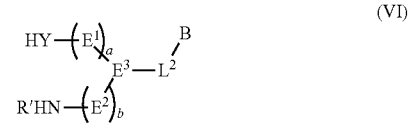

(VI)

wherein each $E^1$ and $E^2$ are independently CHR″, where R″ is a hydrogen, alkyl, alkenyl, alkynyl, cycloalkyl, heterocycloalkyl, aryl, heteroaryl, aralkyl, or a heteroaralkyl group;
   $E^3$ is an alkyl, alkenyl, heteroalkyl, heteroalkenyl, cycloalkyl, heterocycloalkyl, alicyclic system, aryl or heteroaryl group and $E^1$ and $E^2$ are attached to the same or to adjacent carbon and/or nitrogen atoms of $E^3$;
   R' is hydrogen, an alkyl, alkenyl, alkynyl, cycloalkyl, heterocycloalkyl, aryl, heteroaryl, aralkyl, or a heteroaralkyl group;
   Y is S or Se;
   L2 is a linker or a bond;
   B is the second nucleic acid region; and
   one of a and b is 1 and the other one is 0, both a and b are 1, or one of a and b is 2 and the other is 0;

or the second probe comprises a structure

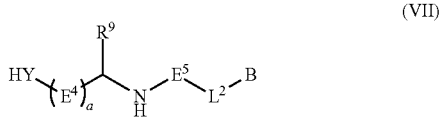

(VII)

wherein each $E^4$ is independently CHR", wherein R" is hydrogen, an alkyl, alkenyl, alkynyl, cycloalkyl, heterocycloalkyl, aryl, heteroaryl, aralkyl, or a heteroaralkyl group;

$E^5$ is CHR" or CR", wherein R'" is hydrogen, an alkyl, alkenyl, alkynyl, cycloalkyl, heterocycloalkyl, aryl, heteroaryl, aralkyl, or a heteroaralkyl group;

$R^9$ is hydrogen, an alkyl, alkenyl, alkynyl, cycloalkyl, heterocycloalkyl, aryl, heteroaryl, aralkyl, or heteroaralkyl group;

Y is S or Se;

$L^2$ is a linker or a bond;

B is the second nucleic acid region; and a is 1 or 2, wherein said first part and said second part of the target nucleic acid sequence are substantially adjacent to each other in the target nucleic acid sequence, wherein the plurality of second probes is associated with one or more nano- or micro-particles, and wherein, in the presence of the target nucleic acid sequence, the first and second probes bind to the first and second parts of the target nucleic acid such that the first reporter group in the first probe is transferred to the second probe; and measuring the presence and/or level of the first reporter group that has been transferred to the second probe.

2. The method according to claim 1, wherein the target nucleic acid sequence is not amplified prior to contacting the sample with the mixture.

3. The method according to claim 1, wherein the method further comprises: isolating the second probe to which the first reporter group was transferred prior to measuring.

4. The method according to claim 1, wherein the one or more of the nano- or micro-particles comprises a gold nanoparticle, a silver nanoparticle, or a microbead.

5. The method according to claim 1, wherein the second probe comprises a second reporter group such that the presence and/or level of the first reporter group that has been transferred to the second probe is measured by measuring the presence and/or level of coexistence of the first reporter and the second reporter on the second probe.

6. The method according to claim 1, wherein the probe set further comprises a third probe, which comprises a third nucleic acid region which is complementary to a third part of the target nucleic acid sequence, the third probe optionally comprising a third reporter group, wherein said third part is substantially adjacent to the first part or the second part of the target nucleic acid sequence.

7. The method according to claim 1, wherein the one or more reporter groups are selected from the group consisting of a fluorescent moiety, a quenching moiety, a donor fluorescent moiety, an acceptor fluorescent moiety capable to fluoresce upon transfer of energy from a donor fluorescent moiety, a radioactive moiety, and a binding moiety.

8. The method according to claim 1, wherein the distance between the first part and the second part of the target nucleic acid sequence is from 0 to 10 nucleotides.

9. The method according to claim 1, wherein the method comprises contacting the sample with one or more additional set of probes, each additional set of probes being configured to hybridize to a different target nucleic acid sequence.

10. The method according to claim 9, wherein each additional set of probes utilizes a different size of nano- or micro-particle.

11. The method according to claim 9, wherein each additional set of probes utilizes a different reporter.

12. The method according to claim 1, wherein the method is implemented in a lateral flow assay device or a two-dimensional paper network device comprising a reaction mixture receiving zone and a detection zone.

13. The method according to claim 12, wherein the presence and/or level of the first reporter is measured in the detection zone.

14. The method according to claim 1, wherein the method is implemented in a microfluidic device.

15. The method according to claim 14, wherein the reaction mixture is provided to a microfabricated channel and the presence and/or level of the first reporter transferred from the first probe to the second probe is measured by a detector operably linked to the microfluidic device.

16. The method according to claim 1 wherein the method is carried out without nucleic acid extraction, amplification and reverse transcription.

17. The method according to claim 1, wherein the sample comprises one or more of a nasopharyngeal swab, nasal aspirate, an oropharyngeal swab, and blood obtained from the subject.

18. A kit for determining the presence and/or level of an analyte comprising a target nucleic acid sequence in a sample, the kit comprising:

a) a plurality of a first probe, the first probe comprising a first reporter group which is capable of being transferred to a second probe, and a first nucleic acid region that is complementary to a first part of the target nucleic acid sequence, wherein the first probe comprises a structure

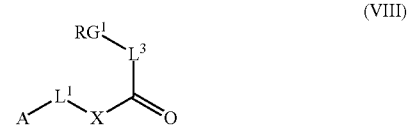

(VIII)

wherein $RG^1$ is the first reporter group;

X is S, O, Se, S—C(O), O—C(O), Se—C(O), or $P^+R^1R^2$, wherein the C(O) group, if present, is bound to $L^1$; $R^1$ and $R^2$, if present, are independently selected from the group consisting of aryl and alkyl;

$L^1$ is a linker or a bond;

$L^3$ is a linker or a bond; and

A comprises the first nucleic acid region, and b) a plurality of a second probe, the second probe comprising a second nucleic acid region complementary to a second, different part of the target nucleic acid sequence, wherein said first part and said second part of the target nucleic acid sequence are substantially adjacent to each other in the target nucleic acid sequence, wherein the second probe comprises a structure

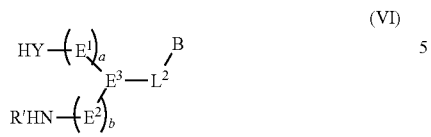
(VI)

wherein each $E^1$ and $E^2$ are independently CHR",
where R" is a hydrogen, alkyl, alkenyl, alkynyl,
cycloalkyl, heterocycloalkyl, aryl, heteroaryl,
aralkyl, or a heteroaralkyl group;

$E^3$ is an alkyl, alkenyl, heteroalkyl, heteroalkenyl,
cycloalkyl, heterocycloalkyl, alicyclic system, aryl
or heteroaryl group and $E^1$ and $E^2$ are attached to the
same or to adjacent carbon and/or nitrogen atoms of
$E^3$;

R' is hydrogen, an alkyl, alkenyl, alkynyl, cycloalkyl,
heterocycloalkyl, aryl, heteroaryl, aralkyl, or a heteroaralkyl group;

Y is S or Se;

L2 is a linker or a bond;

B is the second nucleic acid region; and one of a and b is 1 and the other one is 0, both a and b are 1, or one of a and b is 2 and the other is 0;

or the second probe comprises a structure

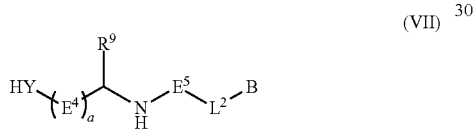
(VII)

wherein each $E^4$ is independently CHR", wherein R" is
hydrogen, an alkyl, alkenyl, alkynyl, cycloalkyl,
heterocycloalkyl, aryl, heteroaryl, aralkyl, or a heteroaralkyl group;

$E^5$ is CHR" or CR", wherein R''' is hydrogen, an alkyl,
alkenyl, alkynyl, cycloalkyl, heterocycloalkyl, aryl,
heteroaryl, aralkyl, or a heteroaralkyl group;

$R^9$ is hydrogen, an alkyl, alkenyl, alkynyl, cycloalkyl,
heterocycloalkyl, aryl, heteroaryl, aralkyl, or heteroaralkyl group;

Y is S or Se;

$L^2$ is a linker or a bond;

B is the second nucleic acid region; and a is 1 or 2, wherein the plurality of second probes is associated with one or more nano- or micro-particles, and wherein binding of the first and second probes to the first and second parts of the target nucleic acid sequence results in the first reporter group in the first probe being transferred to the second probe.

19. The kit according to claim 18, wherein the one or more nano- or micro-particles is selected from the group consisting of a gold nanoparticle, a silver nanoparticle, a microbead, and a mixture thereof.

20. A method of diagnosing a condition in a subject in or substantially near a point of care, the method comprising:
providing a sample obtained from the subject, wherein said sample may comprise an analyte comprising a target nucleic acid sequence associated with the condition;
contacting the sample with a mixture, said mixture comprising at least one set of probes comprising:

a) a plurality of a first probe, the first probe comprising a first reporter which is capable of being transferred to a second probe, and a first nucleic acid region complementary to a first part of the target nucleic acid sequence,
wherein the first probe comprises a structure

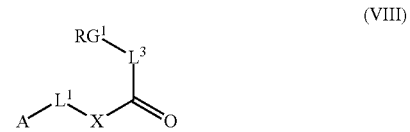
(VIII)

wherein $RG^1$ is the first reporter group;

X is S, O, Se, S—C(O), O—C(O), Se—C(O), or $P^+R^1R^2$, wherein the C(O) group, if present, is bound to $L^1$; $R^1$ and $R^2$, if present, are independently selected from the group consisting of aryl and alkyl;

$L^1$ is a linker or a bond;

$L^3$ is a linker or a bond; and

A comprises the first nucleic acid region, and b) a plurality of a second probe, the second probe comprising a second nucleic acid region complementary to a second, different part of the target nucleic acid sequence, wherein said first part and said second part of the target nucleic acid sequence are substantially adjacent to each other in the target nucleic acid sequence, wherein the second probe comprises a structure

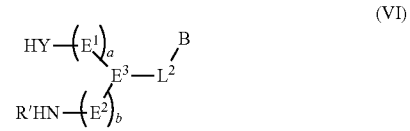
(VI)

wherein each $E^1$ and $E^2$ are independently CHR",
where R" is a hydrogen, alkyl, alkenyl, alkynyl,
cycloalkyl, heterocycloalkyl, aryl, heteroaryl,
aralkyl, or a heteroaralkyl group;

$E^3$ is an alkyl, alkenyl, heteroalkyl, heteroalkenyl,
cycloalkyl, heterocycloalkyl, alicyclic system, aryl
or heteroaryl group and $E^1$ and $E^2$ are attached to the
same or to adjacent carbon and/or nitrogen atoms of
$E^3$;

R' is hydrogen, an alkyl, alkenyl, alkynyl, cycloalkyl,
heterocycloalkyl, aryl, heteroaryl, aralkyl, or a heteroaralkyl group;

Y is S or Se;

L2 is a linker or a bond;

B is the second nucleic acid region; and one of a and b is 1 and the other one is 0, both a and b are 1, or one of a and b is 2 and the other is 0;

or the second probe comprises a structure

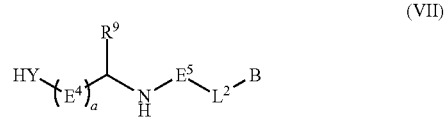
(VII)

wherein each $E^4$ is independently CHR", wherein R" is
hydrogen, an alkyl, alkenyl, alkynyl, cycloalkyl,
heterocycloalkyl, aryl, heteroaryl, aralkyl, or a heteroaralkyl group;

E⁵ is CHR''' or CR''', wherein R''' is hydrogen, an alkyl, alkenyl, alkynyl, cycloalkyl, heterocycloalkyl, aryl, heteroaryl, aralkyl, or a heteroaralkyl group;

R⁹ is hydrogen, an alkyl, alkenyl, alkynyl, cycloalkyl, heterocycloalkyl, aryl, heteroaryl, aralkyl, or heteroaralkyl group;

Y is S or Se;

L² is a linker or a bond;

B is the second nucleic acid region; and a is 1 or 2, wherein the plurality of second probe is associated with one or more nano- or micro-particles;

wherein, in the presence of the target nucleic acid sequence, the first reporter group in the first probe is transferred to the second probe; and measuring the presence and/or level of the first reporter group that has been transferred to the second probe;

wherein the target nucleic acid sequence is not amplified prior to contacting the sample with the mixture.

21. The method according to claim 20, wherein the method further comprises: isolating the second probe to which the plurality of the first reporter group was transferred.

22. The method according to claim 20, wherein the target nucleic acid sequence is associated with one or more selected from the group consisting of dengue virus, influenza virus, chikungunya virus, the human immunodeficiency virus (HIV), the Hepatitis C virus (HCV), Human papillomavirus (HPV), Middle East Respiratory Syndrome (MERS) virus, arboviruses, and methicillin-resistant staphylococcus aureus (MRSA).

23. The method according to claim 20, wherein the target nucleic acid sequence is associated with one or more selected from the group consisting of a bacterium, a fungus and a parasite.

24. The method according to claim 20, wherein the target nucleic acid sequence is associated with nucleic acid biomarkers selected from the group consisting of RNA, DNA, and microRNA in non-communicable and/or chronic diseases.

25. The method according to claim 20, wherein the sample comprises one or more selected from the group consisting of nasopharyngeal swab, nasal aspirate, oropharyngeal swab, and blood obtained from the subject.

* * * * *